United States Patent
Adams et al.

(10) Patent No.: US 11,696,704 B1
(45) Date of Patent: Jul. 11, 2023

(54) SYSTEM, DEVICE AND METHOD FOR TRACKING THE HUMAN HAND FOR UPPER EXTREMITY THERAPY

(71) Applicant: Barron Associates, Inc., Charlottesville, VA (US)

(72) Inventors: Richard J. Adams, Punta Gorda, FL (US); Connor W. Adams, Punta Gorda, FL (US); William T. Gressick, Charlottesville, VA (US); Matthew D. Lichter, Charlottesville, VA (US); Aaron B. Olowin, Charlottesville, VA (US)

(73) Assignee: Barron Associates, Inc., Charlottesville, VA (US)

(*) Notice: Subject to any disclaimer, the term of this patent is extended or adjusted under 35 U.S.C. 154(b) by 435 days.

(21) Appl. No.: 17/007,646

(22) Filed: Aug. 31, 2020

(51) Int. Cl.
*A61B 5/11* (2006.01)
*A61B 5/00* (2006.01)

(52) U.S. Cl.
CPC .......... *A61B 5/1114* (2013.01); *A61B 5/6806* (2013.01); *A61B 5/6812* (2013.01); *A61B 5/744* (2013.01); *A61B 5/486* (2013.01); *A61B 5/6825* (2013.01); *A61B 5/6826* (2013.01); *A61B 2505/09* (2013.01); *A61B 2560/0443* (2013.01);
(Continued)

(58) Field of Classification Search
CPC ... A61B 5/1114; A61B 5/6806; A61B 5/6812; A61B 5/744; A61B 5/486; A61B 5/6825; A61B 5/6826; A61B 2505/09; A61B 2560/0443; A61B 2562/0219; A61B 2562/0223; A61B 5/1071; A63F 13/06; G01L 5/228; G09B 21/009
See application file for complete search history.

(56) References Cited

U.S. PATENT DOCUMENTS 4,414,537 A * 11/1983 Grimes ............... G09B 21/009
 400/479.2
5,810,710 A 9/1998 Burgos
(Continued)

FOREIGN PATENT DOCUMENTS

DE 202005017505 U1 3/2006
WO 2002037466 A1 5/2002
(Continued)

OTHER PUBLICATIONS

Adams, R. J., Ellington, A. L., Armstead, K., Sheffield, K., Patrie, J. T., & Diamond, P. T., "Upper Extremity Function Assessment Using a Glove Orthosis and Virtual Reality System," OTJR: Occupation, Participation and Health, 2019, 39(2), 81-89.

*Primary Examiner* — Patrick Fernandes
(74) *Attorney, Agent, or Firm* — Williams Mullen; Thomas F. Bergert

(57) ABSTRACT

Embodiments of the presently described device, system and method support upper extremity (UE) therapy through tracking the human hand. The system can include a hand-wearable sensor mounting system with hand-wearable components and a movement interpretation circuit. The device can include a hand-wearable component comprising a hook, and a sensing transducer comprising a clip, wherein the clip is detachably securable to the hook. In embodiments, one or more sensing transducers are translationally and rotationally restricted when secured to the hand-wearable components.

23 Claims, 18 Drawing Sheets

(52) U.S. Cl.
CPC ............... *A61B 2562/0219* (2013.01); *A61B 2562/0223* (2013.01)

(56) References Cited

U.S. PATENT DOCUMENTS

| | | | |
|---|---|---|---|
| 7,082,570 B1 * | 7/2006 | von Wiegand | A63F 13/06 |
| | | | 345/161 |
| 7,703,937 B2 | 4/2010 | Shirey | |
| 8,328,744 B2 | 12/2012 | Farrell et al. | |
| 8,371,506 B2 | 2/2013 | Lee | |
| 8,747,002 B2 | 6/2014 | Izkovitz | |
| 8,919,019 B2 | 12/2014 | Martinez et al. | |
| 9,208,565 B2 | 12/2015 | Lee et al. | |
| 9,389,684 B2 | 7/2016 | Sebastian | |
| 9,652,037 B2 | 5/2017 | Rubin et al. | |
| 9,757,266 B2 | 9/2017 | Hoffman et al. | |
| 10,390,575 B2 | 8/2019 | Hull | |
| 10,521,947 B2 | 12/2019 | Yokokawa | |
| 10,610,111 B1 | 4/2020 | Tran | |
| 2007/0270702 A1 | 11/2007 | Ahola | |
| 2010/0234182 A1 | 9/2010 | Hoffman et al. | |
| 2011/0306471 A1 * | 12/2011 | Huang | A61B 5/1114 |
| | | | 482/44 |
| 2014/0215684 A1 * | 8/2014 | Hardy | G01L 5/228 |
| | | | 2/160 |
| 2015/0192413 A1 | 7/2015 | Bellusci et al. | |
| 2018/0335842 A1 | 11/2018 | Rubin et al. | |
| 2019/0204921 A1 | 7/2019 | Goupil et al. | |
| 2019/0357811 A1 * | 11/2019 | Di Pardo | A61B 5/1071 |

FOREIGN PATENT DOCUMENTS

| | | |
|---|---|---|
| WO | 2010085476 A1 | 7/2010 |
| WO | 2015018469 A1 | 2/2015 |

* cited by examiner

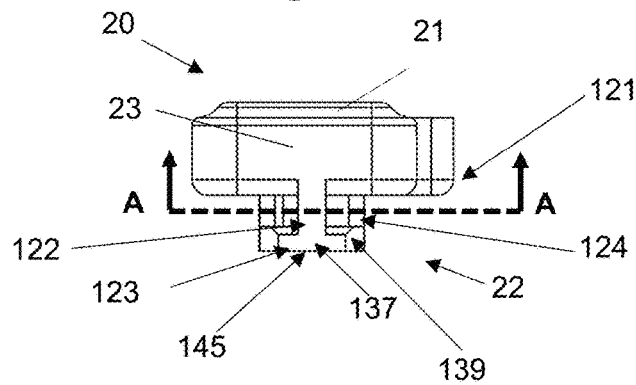
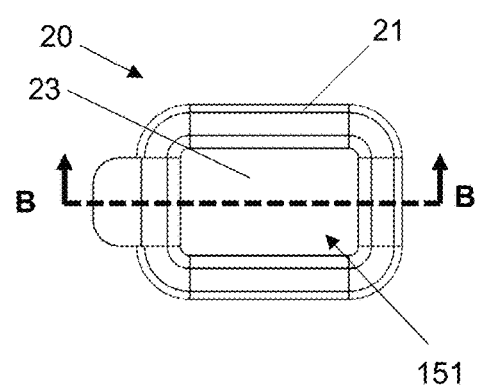
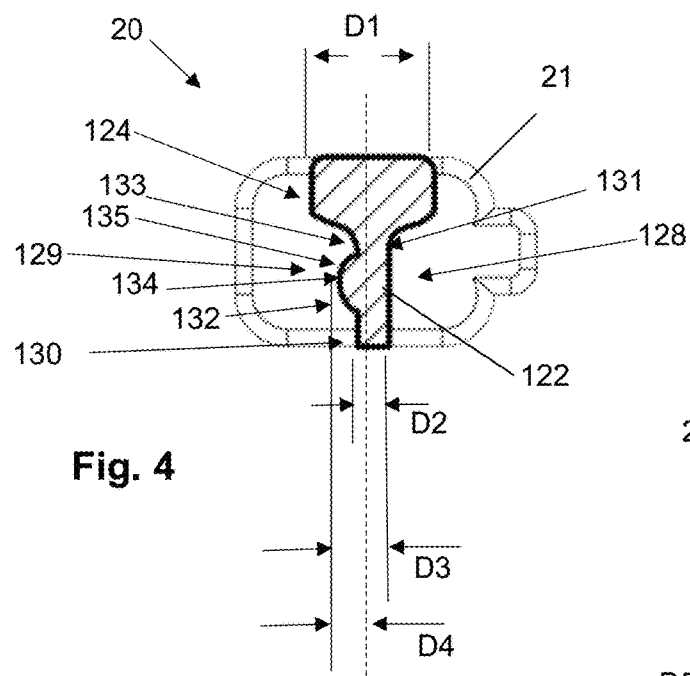
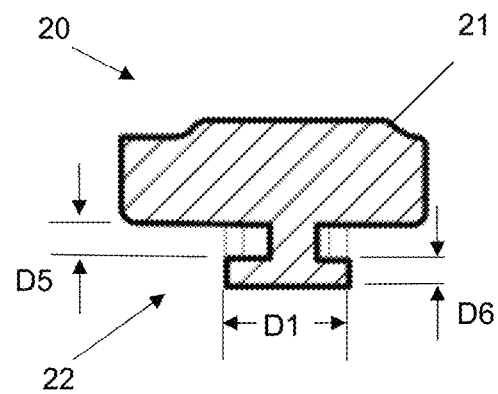

SYSTEM, DEVICE AND METHOD FOR TRACKING THE HUMAN HAND FOR UPPER EXTREMITY THERAPY

STATEMENT

This invention was made with U.S. Government support under grant no. 5R44HD088189-03 awarded by the National Institutes of Health. The Government has certain rights in the invention.

TECHNICAL FIELD

The present disclosure pertains to therapeutic physical rehabilitation, and more particularly to a system, device and method for tracking the human hand as part of upper extremity (UE) therapy.

BACKGROUND AND SUMMARY

The scope of the healthcare challenge posed by neurological (e.g. stroke and head trauma) and orthopedic injuries is massive. From stroke alone, there are approximately 900,000 hospitalizations per year in the U.S., representing approximately eighty stays per 10,000 persons over forty-five years of age. Approximately fifty percent of these individuals suffer from chronic deficits in UE function, including hand motor control deficits that can diminish the ability to participate in daily activities.

UE therapy is intended to help a patient reacquire the functional skills necessary to perform practical tasks and to address underlying deficits which can include lack of hand strength, poor motor control, and limited range of motion. Existing research evidence has shown that the dosage of practice plays a primary role in affecting positive outcomes in therapy. Virtual world-based computer games and other electronic games can provide a means to maintain patient engagement while delivering high-dosage evidence-based rehabilitation. A critical deficiency in existing computer game-based solutions for UE therapy is that they do not adequately address the need for practice involving dexterous use of the hand, which requires tracking of hand and finger movements. Existing therapy software systems that use motion capture cameras, such as the Microsoft Kinect™ for Xbox One™, for example, provide exercise for the shoulder and elbow, but not for the hand.

Existing wearable systems for tracking the movement of a human hand are not easily sanitized, are not easily adaptable to different hand sizes and handedness, are not stable yet versatile, and cannot be used with multiple sensor mounting systems that are adapted to the needs of the application (e.g., therapy or gaming) or the patient's functional ability (e.g., a patient that needs wrist support or finger extension assistance due to weakness versus a patient that does not require such support).

The present disclosure addresses the above and other technological challenges. In part, the present disclosure provides a device for securely yet removably attaching sensors to a human hand, a system for tracking the movement of a human hand, and a computer-implemented method of human UE therapy, enabling the human hand to be tracked in a system for computer-guided UE therapy for recovery from neurological or orthopedic injury. When combined with a virtual world-based software application for the practice of activities of daily living (ADLs) and instrumental ADLs (IADLs), embodiments of the present disclosure support a difficulty- and dosage-scalable solution for in-clinic and home-based UE therapy. Embodiments of the present disclosure can also be used for virtual reality and gaming applications, or in any computer application requiring tracking of the human hand. For example, embodiments of the present disclosure can be used to track the usage of a hand (movement repetition and range of motion) over the course of a day by a patient as he or she goes about his or her normal daily activities.

Embodiments of a system for tracking the movement of the hand of a human as described herein can include a movement interpretation circuit and a hand-wearable sensor mounting system with multiple hand-wearable components. The movement interpretation circuit can include sensing transducers that are communicatively coupled to an information system and/or computing device or system that interprets the movements of sensing transducers as the movement of a human hand and/or a human finger. In certain exemplary embodiments, the movement interpretation circuit can include a microcontroller. Sensing transducers can be employed and operatively configured to securely attach to the hand-wearable sensor mounting system using an interlocking clip on the sensing transducers that mates to a corresponding interlocking hook on one or more of the hand-wearable components of the hand-wearable sensor mounting system. The movement interpretation circuit can automatically interpret the movements of the sensing transducers as the actual hand and finger movements of a human.

Embodiments of a device for securely attaching sensors to the human hand according to the present disclosure can include a hand-wearable component operatively configured to receive and stably retain detachable sensing transducers. The hand-wearable component can include an interlocking hook and the sensing transducer can include an interlocking clip. The interlocking elements permit the detachable sensing transducers to be securely attached to the human hand and further can be used in a system for tracking the movement of the human hand when combined with a movement interpretation circuit as described elsewhere herein. The interlocking elements permit the detachable sensing transducers to be easily attached and detached, while also maintaining a compact form for ease of attachment, detachment and use. The interlocking elements also restrict translational and rotational movement of the sensing transducer when secured to the hand-wearable component, which facilitates proper operation and movement sensing for UE therapy. The detachability of the sensing transducers provides critical benefits, including: the hand-wearable component can be easily separated from the detachable sensing transducers for washing/sanitizing; the same detachable sensing transducers can be employed by either right or left handed patients; the same detachable sensing transducers can be employed with hand-wearable components of different sizes (e.g. small, medium, or large hands); the same detachable sensing transducers can be used by different patients; and the same detachable sensing transducers can be used with different embodiments of hand-wearable components, including rings, dorsal mounts, and gloves formed with interlocking elements, for example.

In certain exemplary embodiments, hand-wearable components include a ring and a dorsal mount operatively configured with an interlocking hook that mates to an interlocking clip on detachable sensing transducers. Embodiments of the ring can include a ring upper section, operatively configured with an interlocking hook that mates to a clip on the detachable sensing transducers. Embodiments of the dorsal mount can be designed to attach to the hand in the first dorsal interosseous region between the index finger and the thumb and be attached using a fabric strap with hook-and-loop fastener. The design of the dorsal mount takes advantage of the fact that the dorsal interosseous region of the hand is relatively immobile during finger and thumb flexion and extension movements and during wrist flexion, extension, abduction, and adduction movements that may be exercised during UE therapy, thus allowing the dorsal mount to provide a stable platform for detachable sensing transducers. In exemplary embodiments, the use of a fabric strap around the hand to secure the dorsal mount to the human hand prevents the device from interfering with normal use of the hand (e.g. to pick up, manipulate, and use objects).

In certain exemplary embodiments, the hand-wearable component is a glove formed with one or a plurality of interlocking hooks to which detachable sensing transducers can be mated. The location of interlocking hooks on the glove can include placement above the proximal, intermediate, or distal phalanges of any finger or thumb, or any other location on the glove that may move during UE therapy.

Certain exemplary embodiments involve repurposing securing elements on a SaeboGlove™ commercial glove orthosis as mating elements for the interlocking clip on detachable sensing transducers as described herein. The securing elements of the SaeboGlove™ are designed by its manufacturer, Saebo, Inc. of Charlotte, N.C., to support elastic tensioner bands providing finger extension assistance. As described in connection with embodiments herein, the securing elements on the glove orthosis are repurposed to serve as interlocking elements to which the interlocking clip on a detachable sensing transducer according to the present disclosure can be mated, thus allowing the sensors to be securely attached and used as part of a movement interpretation circuit for tracking of the human hand. The combined system can thereby be used to engage the hand in exercise during computer-guided UE therapy.

In certain exemplary embodiments, detachable sensing transducers can include any combination of one or more accelerometers, gyroscopes, and/or a geomagnetic sensors (magnetometers). In certain exemplary embodiments, detachable sensing transducers can include a Bosch BMF055 9-axis motion sensor module (which can include a triaxial 14-bit accelerometer, a triaxial 16-bit gyroscope, and a triaxial geomagnetic sensor) providing sensor measurement of orientation, rotational velocity, and translational acceleration at the location of each detachable sensing transducer secured to the human hand using hand-wearable components.

In certain exemplary embodiments, a system for tracking the movement of the hand of a human as described herein can include a hub unit that houses components of a movement interpretation circuit that can include a 32-bit Nordic microcontroller and a Bosch BMF055 9-axis motion sensor module that is communicatively coupled to the microcontroller. The microcontroller in the hub unit can be communicatively coupled to detachable sensing transducers through a wiring harness. In certain exemplary embodiments, the microcontroller can wirelessly transmit sensor measurements from the movement interpretation circuit to an information system and/or computing device or system using a transceiver module housed in the hub unit, such as via Bluetooth. In certain exemplary embodiments, the hub unit can be attached to the wrist of a human using a fabric strap with hook-and-loop fastener. In certain exemplary embodiments, the hub unit can be mounted to a wrist-immobilizing splint such as that used in the SaeboGlove™ orthosis.

In certain exemplary embodiments, the hub unit can include sensory output transducers. Sensory output transducers can include an eccentric rotating mass (ERM) vibrotactile motor operatively configured within the enclosure such that generated vibrations can be perceived by a user. In certain exemplary embodiments, the transceiver module can wirelessly receive data from a computer specifying tactile sensory cues to be generated by the vibrotactile motor. The microcontroller can process these data into commands to a haptic driver integrated circuit (IC) to provide electrical current to the vibrotactile motor to achieve a desired vibrotactile effect. In certain exemplary embodiments, tactile sensory cues can include pulses by the vibrotactile motor of specified number, duration, amplitude, and inter-pulse delay.

In certain exemplary embodiments, the hub unit's sensory output transducers can include one or a plurality of red, green, and blue (RGB) light-emitting diodes (LEDs). In certain exemplary embodiments, the transceiver module can wirelessly receive data from a computer specifying light effect sensory cues to be generated by the LEDs. The microcontroller in the hub unit can process these data into commands to an IC to achieve a desired color hue and intensity. In certain exemplary embodiments, light effect sensory cues can include pulses by one or more of the RGB LEDs of specified number, color, intensity, duration, and inter-pulse delay.

In certain exemplary embodiments, a computer-implemented method of human UE therapy can involve providing a device comprising a plurality of hand-wearable components and at least one sensing transducer detachably secured to at least one of the plurality of hand-wearable components, sensing the movement of a human hand wearing the plurality of hand-wearable components, conveying the sensed movement of the hand to a computing device and executing, by the computing device, instructions stored in a memory to display movement of a virtual object on a visual display based on the sensed movement. In certain exemplary embodiments, sensor measurement data for tracked hand movement can be automatically interpreted as movements of a human avatar in a virtual world.

Sensor measurement data provided to a computer can include the measured orientation, rotational velocity, and translational acceleration of each sensing transducer at the location of a hand-wearable component on a human hand. These data can be processed by a sensor data interpretation algorithm to produce human kinematic state estimates.

Human kinematic state estimates provided by the sensor data interpretation algorithm to a computer can be interpreted as the kinematic state of the UE of a human avatar within a three-dimensional virtual world, in various embodiments. The movement of the UE of a human avatar in a virtual world can thus be made to follow the UE movement of a human wearing a system for tracking the movement of the hand of a human, as described in the present disclosure. A virtual world can be formed with a virtual world interactivity model to simulate environments and activities that are relevant to UE therapy. The virtual world interactivity model can interpret the interactions between a human avatar and other objects in the virtual world to create virtual object interactions that result in therapeutic exercise of the human UE. Virtual world interactions resulting in therapeutic exercise can include picking up, translating, rotating, placing, dropping, throwing, and squeezing objects within virtual world activities such as grocery shopping, putting away groceries, preparing breakfast, pet shopping, pet feeding, pet bathing, garden planting, garden harvesting, preparing dinner, organizing a closet, and eating, for example. Objects within virtual world activities can include grocery items, pet care items, self-care instruments, utensils, clothing, drawers, cabinets, and appliances, for example.

Virtual world interactions between a human avatar and other objects in the virtual world can be processed by a virtual world object model to produce changes in the state of the virtual world. These changes can include changes to the position, velocity, orientation, and depiction of virtual objects, as well as effects such as filling of a virtual glass with water, a piece of virtual food being consumed, for example. The state of the virtual world can be communicated to a human through sensory output transducers which can include a visual sensory output transducer, an audio sensory output transducer, and a haptic sensory output transducer, for example.

In certain exemplary embodiments, a human motion capture device can be used with a system for tracking the movement of the hand of a human. In certain exemplary embodiments, the human motion capture device can include a depth sensor camera and skeletal tracking software. A human motion capture device can be operatively configured to sense the position of the joints of a human arm and hand, and to transmit human motion capture data to a sensor data interpretation algorithm. A sensor data interpretation algorithm can interpret data provided by the human motion capture device in combination with a system for tracking the movement of the hand to provide human kinematic state estimates that include estimated joint angles, joint angular rates, joint positions, and joint velocities for joints of the human arm (shoulder and elbow), in addition to the joints of the hand. It will be appreciated that a computing device can interpret these human kinematic state estimates as the shoulder, elbow, and hand states of the UE of a human avatar within a three-dimensional virtual world.

BRIEF DESCRIPTION OF THE SEVERAL VIEWS OF THE DRAWINGS

FIG. 2 shows a side view of a detachable sensing transducer with an interlocking clip in accordance with embodiments of the present disclosure.

FIG. 3 shows a top view of a detachable sensing transducer with an interlocking clip in accordance with embodiments of the present disclosure.

FIG. 4 is a cross-section taken along the line A-A of FIG. 2.

FIG. 5 is a cross-section taken along the line B-B of FIG. 3.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Where computing elements are involved, a system and/or device may be implemented as a single computing device or system or as a collection of computing devices, systems or subsystems which are communicatively coupled, directly or indirectly, and each component or subsystem of the exemplary device and/or system can be implemented in hardware, software or a combination thereof. In various embodiments, the system and/or device each have a processor and an associated memory storing instructions that, when executed by the processor, cause the processor to perform operations as described herein. It will be appreciated that reference to "a", "an" or other indefinite article in the present disclosure encompasses one or more than one of the described element. Thus, for example, reference to a processor encompasses one or more processors, reference to a sensing transducer represents one or more sensing transducers, reference to a strap represents one or more straps, and so forth.

Figure 1:
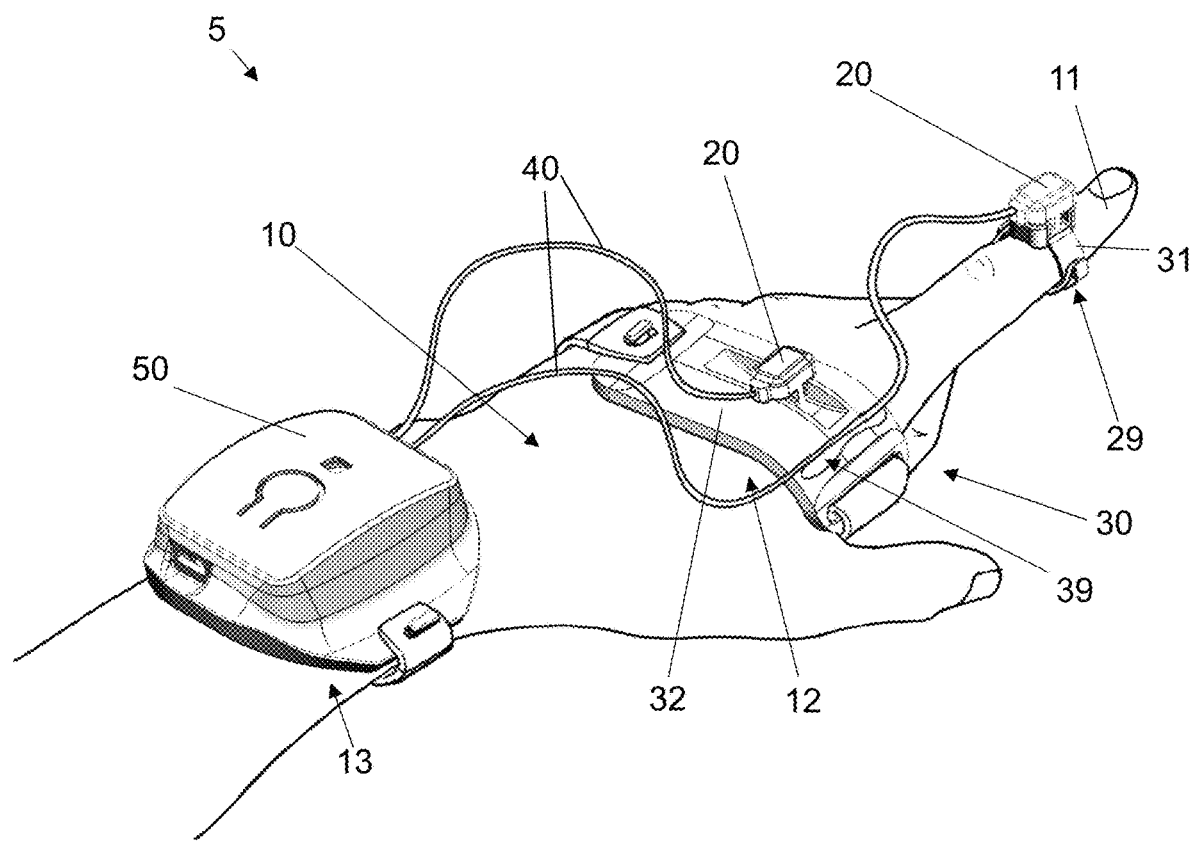
FIG. 1 shows a perspective view of a system for tracking the movement of the hand in accordance with embodiments of the present disclosure.

As shown in FIG. 1, a system 5 for tracking the movement of the human hand 10 is provided with detachable sensing transducers 20 and hand-wearable components 29, 30. A wiring harness 40 communicatively couples the sensing transducers 20 to a hub unit 50. Hand-wearable component 29 is a finger sensor mount worn on a human finger 11. In certain exemplary embodiments, the finger sensor mount can be a hand-wearable ring component 31, as shown in FIG. 1. In certain exemplary embodiments, hand-wearable component 30 can include a hand-wearable dorsal mount component 32 securable about the dorsal interosseous region 12 of the human hand 10. In certain exemplary embodiments, the hub unit 50 can be considered a hand-wearable component and can be worn on the human wrist 13. In certain exemplary embodiments, a cable retention channel 39 is formed in the hand-wearable component 30 and can secure a cable of the wiring harness 40, such as the cable from the ring component 31 therein. Embodiments of the dorsal mount component 32 take advantage of the fact that the dorsal interosseous region of the hand is relatively immobile during finger and thumb flexion and extension movements and during wrist flexion, extension, abduction, and adduction movements that may be exercised during UE therapy, thus allowing the dorsal mount component 32 to provide a stable platform for detachable sensing transducers. The use of a fabric strap around the hand to secure the dorsal mount component 32 to the human hand prevents the device from interfering with normal use of the hand (e.g., to pick up, manipulate, and use objects). A fabric strap can also be used to secure the hub unit 50 around the wrist 13.

As shown in FIGS. 2 through 5, an exemplary detachable sensing transducer 20 can be formed with a sensor housing 21, a motion sensor module 23, and an interlocking clip 22. The clip 22 has a head portion 121, a neck portion 122, a base portion 123 and a back wall 124. The back wall 124 extends from the head portion 121 to the base portion 123 and is provided of a sufficient width D1 to act as a stopping surface when the transducer 20 is interlocked with a hand-wearable component (e.g., 29, 30 in FIG. 1). The neck portion 122 is formed with a first side wall 128 having a mid-wall segment 131, and a second side wall 129 having a leading wall segment 130, a knob 132 and a mid-wall segment 133, wherein the leading wall segment 130 and mid-wall segment 133 can be provided with a width D2 that is narrower than width D1. The first side wall 128 of the neck portion 122 is substantially planar, and the knob 132 of the second side wall 129 is formed so as to extend outwardly from the second side wall 129 between the leading segment 130 and the mid-wall segment 133.

The knob 132 can be provided with a crest 134 having a crest width D3 measured from the first side wall 128 to the crest 134 that is wider than width D2 but narrower than width D1. In various embodiments, the knob 132 is rounded at its outer surface 135 so as to provide a gradually increasing and/or decreasing surface contact area for interoperability with hook 33 of a hand-wearable component (e.g., 29, 30 in FIG. 1). In this way, and as the crest width D3 is larger than the gap width D9 of the hook 33 as described elsewhere herein, the knob 132 can act as a latching mechanism to secure the sensing transducer 20 in interlocking relation with various embodiments of the hand-wearable component (e.g., 29, 30 in FIG. 1) as described more completely elsewhere herein.

Figure 9:
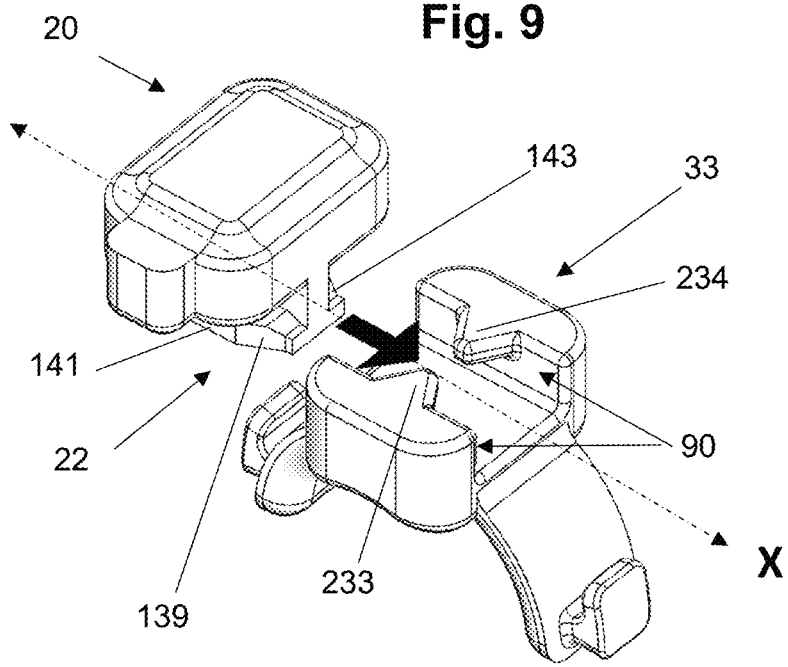
FIG. 9 illustrates the mating of a detachable sensing transducer with a hand-wearable ring component with an interlocking clip and an interlocking hook in accordance with embodiments of the present disclosure.
Figure 12:
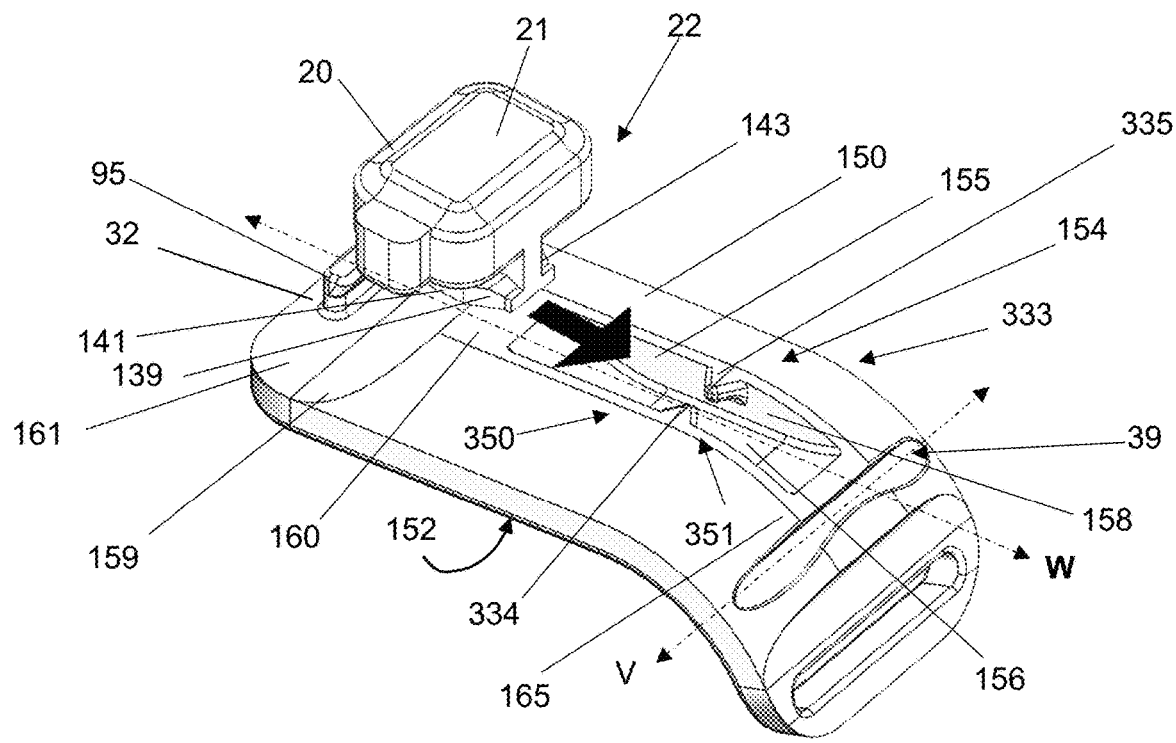
FIG. 12 is a perspective view illustrating the mating of a detachable sensing transducer with a hand-wearable dorsal mount component with an interlocking clip and an interlocking hook in accordance with embodiments of the present disclosure.

As shown in FIGS. 2 through 5, 9 and 12, and as described elsewhere herein, the interlocking clip 22 can be provided with a geometric shape that allows it to detachably mate with an interlocking element on various types of hand-wearable components such as shown at 29, 30. For example, the base portion 123 of the clip 22 can be provided with a leading face 137 and angled side walls 139 extending laterally outwardly from the leading face 137 to a body portion 141. The base portion 123 can further be provided with angled and/or chamfered top edges 143 extending upwardly away from the leading face 137 and towards the body portion 141 of the base portion 123 of the clip 22, as shown in FIGS. 9 and 12. The angled side walls 139 and angled top edges 143 assist in guiding the clip 22 into position when the transducer 20 is being attached to and/or detached from a hand-wearable component (e.g., 29, 30 in FIG. 1). In FIG. 2, the base portion 123 is shown with a flat bottom surface 145. However, it will be appreciated that embodiments of the present disclosure can employ a rounded bottom surface or other shaped surface to facilitate interlocking engagement with hand-wearable components (e.g., 29, 30 in FIG. 1).

Figure 6:
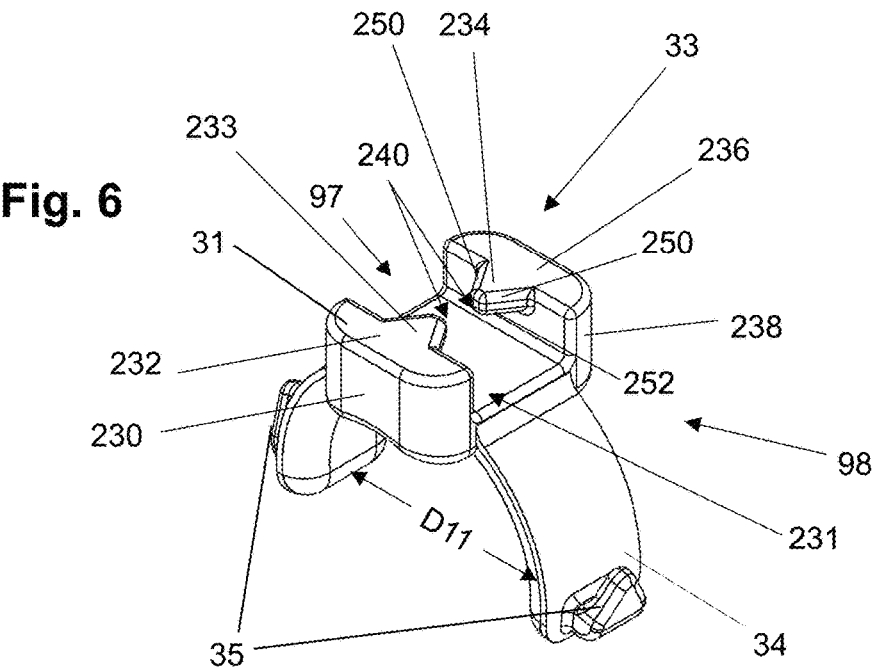
FIG. 6 shows a perspective view of a hand-wearable ring component with interlocking hook in accordance with embodiments of the present disclosure.
Figure 7:
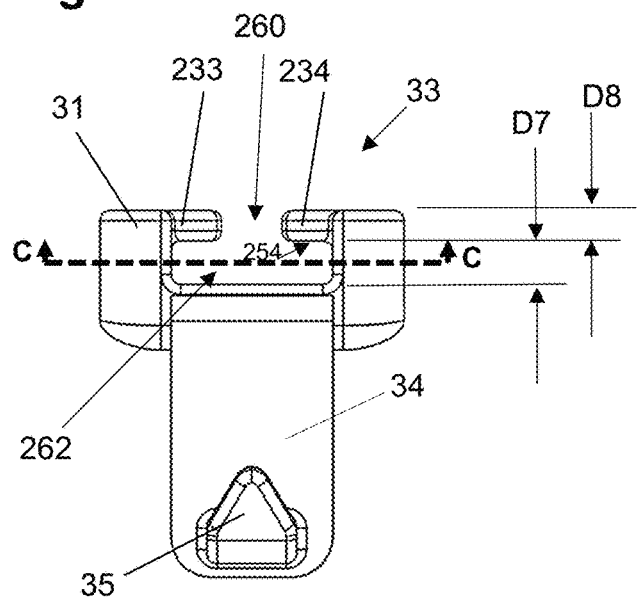
FIG. 7 shows a side view of a hand-wearable ring component with interlocking hook in accordance with embodiments of the present disclosure.
Figure 8:
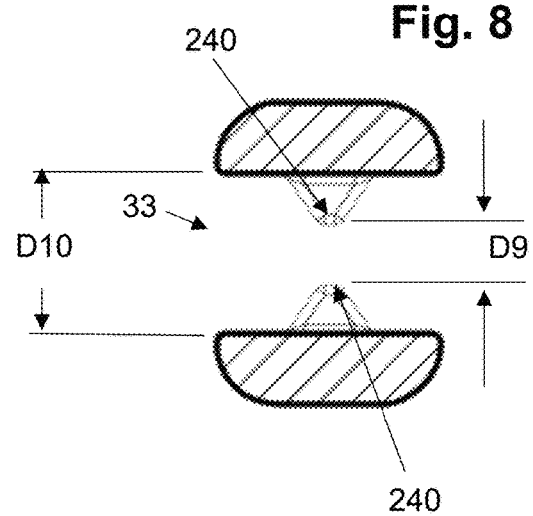
FIG. 8 is a cross-section taken along the line C-C of FIG. 7.

As shown in FIGS. 6 through 8, the hand-wearable ring component 31 can be formed with an interlocking hook 33, a ring band 34, and an elastic band retainer 35. In various embodiments, hook 33 is formed as a pair of diametrically opposed hook elements 233, 234 formed with a gap 260 therebetween. The first hook element 233 extends outwardly from a first horizontally extending top wall 232 of the ring component 31, wherein the top wall 232 is formed with a first side wall 230 of the ring component 31, wherein the first side wall 230 extends vertically upwardly from a ring component floor 231. The second hook element 234 extends outwardly from a second horizontally extending top wall 236 of the ring component 31, wherein the top wall 236 is formed with a second side wall 238 of the ring component 31, wherein the second side wall 238 extends vertically upwardly from the ring component floor 231, and further wherein the first hook element 233 and the second hook element 234 extend toward one another. Each hook element 233, 234 can be formed with angled side walls 250 such that the hook elements 233, 234 extend away from the respective top walls 232, 236 to a point 240. The pointed edge of each hook element 233, 234 can facilitate attaching and detaching a sensor transducer 20 to the hook 33 as the point 240 creates more room for maneuverability by the user's hand. Further, each hook element 233, 234 can be formed with beveled edges 252, wherein each beveled edge 252 extends from a respective angled side wall 250 downwardly and inwardly toward a bottom surface 254 of the hook element 233, 234. In this way, the hook elements 233, 234 provide for smoother engagement and interlocking with the clip 22 of an inserted transducer 20. The ring upper section can be fabricated from plastic, metal, or any other suitable material. The ring upper section can include additional interlocking hook elements that support an elastic band that secures the ring to a human finger. By using elastic bands of different sizes, the ring can be adapted to be comfortably worn on fingers of different sizes. The use of the elastic band also prevents the ring from interfering with normal use of the hand (e.g., for pickup up and manipulating objects) while the ring is worn.

Figure 10:
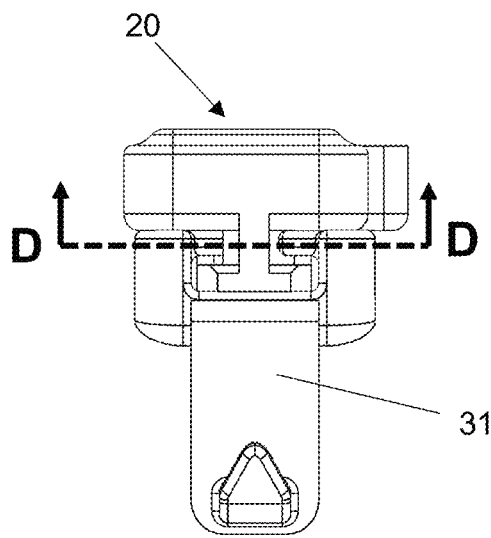
FIG. 10 shows a side view of a hand-wearable ring component for securing a detachable sensing transducer to a finger on a human hand in accordance with embodiments of the present disclosure.
Figure 11:
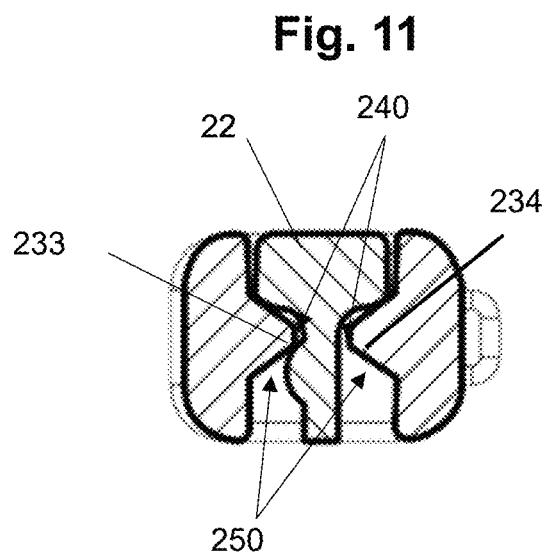
FIG. 11 is a cross-section taken along the line D-D of FIG. 10.

As shown in FIGS. 9 through 11, the interlocking clip 22 on a sensing transducer 20 can be inserted into the interlocking hook 33 on the ring hand-wearable component 31 along axis X. In so doing, it will be appreciated that the angled side walls 139 and top edges 143 of the clip 22 facilitate smooth engagement with hook 33 and the interior wall surface 90 of the ring component 31. As described elsewhere herein, the sensing transducer neck portion width D2 is smaller than the gap width D9 of the hook 33 of the hand-wearable component 29, 30 so that the neck portion 122 can pass through the gap 260 between the pair of opposing hook elements 233, 234 as the sensing transducer is detachably secured to the hook 33. FIG. 10 shows a side view of a detachable sensing transducer 20 that has been fully inserted into hand-wearable ring component 31. FIG. 11 shows a cross-sectional view taken along the line D-D from FIG. 10. As can be seen in FIGS. 9 through 11, when the clip 22 is inserted, the knob 132 of the neck portion 122 of the transducer housing 21 is pushed past the points 240 of the hook 33 such that the points 240 of the hook 33 engage the mid-wall 133 of the neck portion 122 and thereby lock the inserted clip 22 in place. Further, the back wall 124 of the housing 21 engages the angled side edges 250 of the inserted side of the hook 33 to provide a stopping force on the entry of the inserted clip 22. It will be appreciated that, by forming the interlocking clip 22 and interlocking hook 33 such that dimension D4 in FIG. 4 is greater than one half of dimension D9 in FIG. 8, the interlocking clip 22 will be securely mated to the interlocking hook 33 when fully inserted along axis X. In other words, the knob 132 extends sufficiently laterally outward from the neck portion 122 between the leading wall 130 and the mid-wall 133 such that the knob 132 may collide with one point 240 of the hook 33 and snap past the point 240 when inserted. Once the knob 132 passes the hook elements 233, 234, the clip 22 is forced to be centered by the surfaces on the clip and the angled edges forming the points 240 on the hook elements 233, 234. In various embodiments, a second knob can be provided on the first side 128 of the neck portion 122. The second knob can be diametrically opposed from knob 132 or may be staggered such that knob 132 encounters the point 240 of hook element 233 and the second knob encounters the point 240 of hook element 234 at different times when the transducer 20 is inserted into a hand-wearable component (e.g., 29, 30, 31).

It will further be appreciated that by forming interlocking clip 22 and interlocking hook 33 such that dimension D3 in FIG. 4 can be just greater than dimension D9 in FIG. 8 so that the knob 132 snaps past the points 240 as described above, regardless of whether the detachable sensing transducer 20 is being attached or detached from the hand-wearable component 29, 30. Further, it will be appreciated that, in accordance with various embodiments, base portion width D1 is less than the width D10 between side walls 90 of the hook 33, such that the base portion 123 can be inserted into a slot 262 as will be described hereinafter. Base portion and back wall width D1 is also wider than gap width D9 so that the user cannot push the base portion 123 through the gap 260 but is rather guided to align the neck portion 122 of the clip 22 with the gap 260, while back wall 124 also acts as a stopping surface against hook elements 233, 234. The slot 262 is bounded by hook elements 233, 234, floor surface 231 and opposing side walls 90. The slot 262 has a slot height D7 and the clip base portion height D6 is less than the slot height D7 so that the base portion 123 can move through the slot 262 during operation. The neck portion width D2 is less than gap width D9 such that neck portion 122 can extend between hook elements 233, 234 and such that mid-wall segments 131, 133 can be detachably retained by the hook element 233, 234. The neck portion height D5 is greater than hook element height D8 such that the clip 22 can slide past hook points 240. Also, base portion height D6 is less than slot height D7 such that the clip 22 can slide past hook points 240. It will be appreciated that the clip head portion 121 has a bottom surface 151 that can slidingly engage the top surfaces 232, 236 of the opposing hook elements 233, 234 as the sensing transducer 20 is detachably secured to the hook 33. The hook 33 on ring component 31 can be considered as having multiple sides 97, 98 for entry of the sensing transducer, which contributes to its ease of use and versatility. Further, by providing the elements and geometries described herein, in full or in part, the clip 22 is translationally and rotationally restricted by the hook 33 when the clip 22 is secured to the hook 33. In various embodiments, the translational and rotational restriction results in the inability of the sensing transducer 20 to move with respect to the hand-wearable component 29, 30 unless the sensing transducer 20 is detached from the hand-wearable component 29, 30.

Other arrangements that restrict the translational and rotational movement of the sensing transducer 20 with respect to the hand-wearable component 29, 30 can be employed and are contemplated by the present disclosure. Such other arrangements can include, for example, multiple snapping components such as two male or female snap components on the bottom surface of the sensing transducer 20 and two female or male (necessarily the opposite form from that on the sensing transducer) snap components on a top surface of the hand-wearable component 29, 30. In such form, the snap components on the sensing transducer 20 can be considered a clip and the snap components on the hand-wearable component 29, 30 can be considered a hook. Other arrangements can include an open compartment secured to a top surface of the hand-wearable component wherein the dimensions of the sensing transducer 20 or a portion thereof are sufficiently large in comparison to the dimensions of the open compartment so as to provide a friction fit with the compartment when the sensing transducer 20 or portion thereof is inserted in the compartment. In such arrangement, the elements of the sensing transducer 20 that help create the friction fit can be considered the clip and the elements of the compartment of the hand-wearable component 29, 30 that help create the friction fit can be considered the hook. Still other arrangements can include an open compartment secured to a top surface of the hand-wearable component 29, 30 with a cantilevered snap latch extending from one or more surfaces of the compartment. The sensing transducer 20 can be placed in the compartment and provided with a housing of sufficient dimension to fit within the open compartment and permitting the snap latch to snap into place upon insertion of the sensing transducer 20 within the open compartment. When the sensing transducer 20 is to be removed, the snap latch can be manually pulled back to enable the sensing transducer 20 to be easily pulled from the compartment on the hand-wearable component 29, 30. In such an arrangement, the elements of the sensing transducer 20 that help create the fit within the compartment can be considered the clip and the cantilevered snap latch of the hand-wearable component 29, 30 can be considered the hook. Other arrangements incorporating snap-latch mechanisms on one or both of the hand-wearable component 29, 30 and the sensing transducer 20 can be employed so as to restrict translational and rotational movement such that the sensing transducer 20 is unable to move with respect to the hand-wearable component 29, 30 unless the sensing transducer 20 is detached from the hand-wearable component 29, 30.

Figure 13:
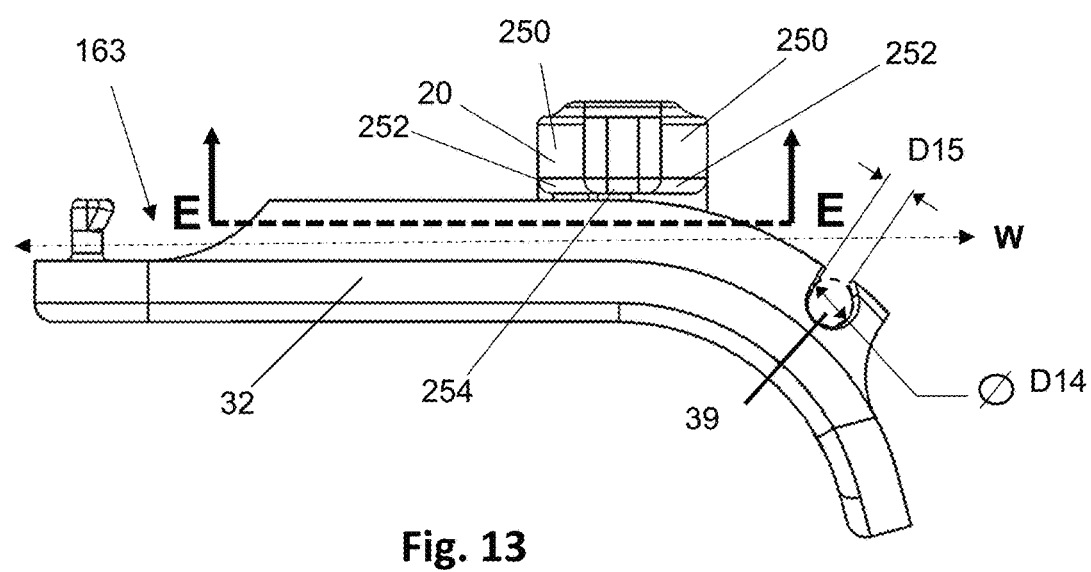
FIG. 13 shows a side view of a device for securing a detachable sensing transducer to a dorsal mount component in accordance with embodiments of the present disclosure.
Figure 14:
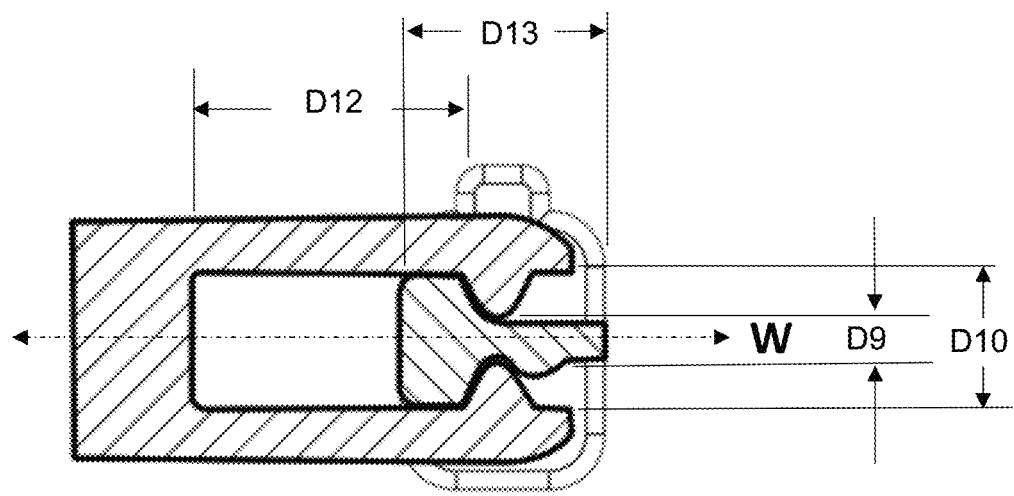
FIG. 14 is a cross-section taken along the line E-E of FIG. 13 when the sensor is oriented for right hand use.
Figure 15:
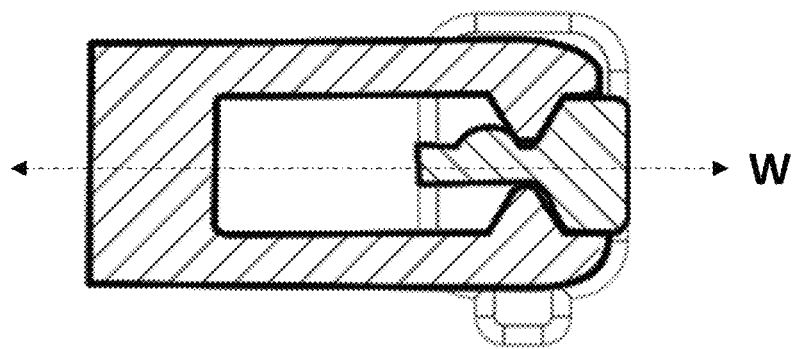
FIG. 15 is a cross-section taken along the line E-E of FIG. 13 when the sensor is oriented for left hand use.

As shown in FIG. 12, the interlocking clip 22 on detachable sensing transducer 20 can be inserted into the interlocking hook 33 on the hand-wearable dorsal mount component 32 along axis W. FIG. 13 shows a side view of detachable sensing transducer 20 after it has been fully inserted into hand-wearable dorsal mount component 32. FIGS. 14 and 15 show a cross-sectional view taken along the line E-E from FIG. 13. In FIG. 14, the detachable sensing transducer 20 is oriented for right hand use. In FIG. 15, the detachable sensing transducer 20 is oriented for left hand use.

In various embodiments as shown in FIGS. 12 through 15, the hand-wearable dorsal mount component 32 can be provided with a base 150 wherein the underside 152 of the base 150 contacts the user's hand when installed. A slot 155 can be formed in the top surface 154 of the base 150, wherein the slot 155 is defined by a slot floor 156 and slot walls 158. A hook 333 is provided in similar fashion to hook 33 in FIGS. 6 through 11, where opposing hook elements 334, 335 are formed to receive the transducer 20 and clip 22. A band retention element 95 can be secured to a platform 161 on the top surface 154 of the base 150 in order to securely retain a hand strap 38 as described elsewhere herein. The top surface 154 of the base 150 can further be formed with a swale 159, a bridge 160 and a clearance gap 163 to facilitate attachment of the hand strap 38 to the band retention element 95 and further to provide room for the user's hand and the transducer 20 when securing the transducer to the dorsal mount component 32. In various embodiments, the bridge 160 lies coplanar with the top surface 154 of the base 150, and the swale 159 slopes or curves downwardly from the bridge 160 to a platform 161 to which the band retention element 95 is secured. The hook 333 can be considered as having multiple sides 350, 351 for entry of the sensing transducer, which contributes to its ease of use and versatility.

It will be appreciated that, in various embodiments, dimension D13 is less than dimension D12, which permits the interlocking clip 22 to be inserted into the interlocking hook 33 for right hand use. As shown in FIGS. 12 and 13, the hand-wearable dorsal mount component 32 can be formed with a cable retention channel 39 as described elsewhere herein. In various embodiments, the cable retention channel 39 is spaced apart from slot 150 by a channel gap 165 on the top surface 154 of the base 150 of the dorsal mount component 32. The channel gap 165 ensures that there is adequate surface area in the cable retention channel 39 to retain an inserted cable. It will be appreciated that, by making the inner diameter D14 of the cable retention channel 39 larger than the outer diameter of the cable used in the wiring harness 40, the cable will slide freely along direction V when the hand is opened and closed. It will be appreciated that, by making the entry gap width D15 of the cable retention channel 39 less than the outer diameter of the cable used in the wiring harness 40, the cable will be held proximal to the hand-wearable dorsal mount component 32.

Figure 16:
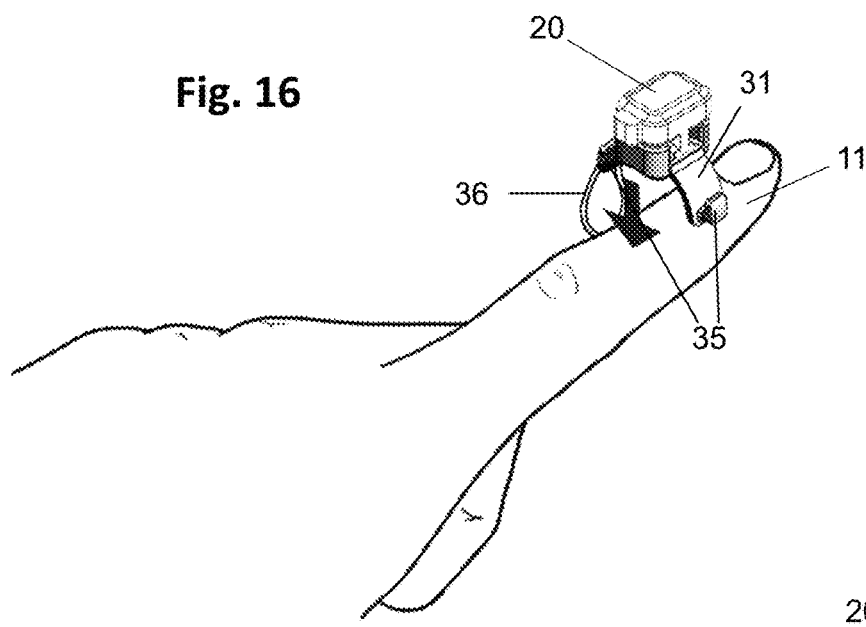
FIG. 16 shows a perspective view illustrating placement of a hand-wearable ring component with a detachable sensing transducer on a human finger in accordance with embodiments of the present disclosure.
Figure 17:
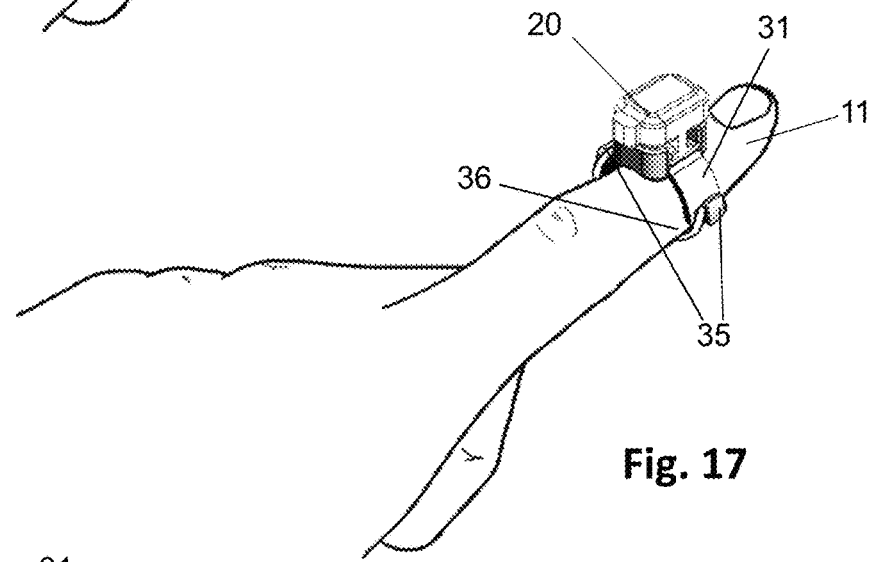
FIG. 17 shows a perspective view illustrating a hand-wearable ring component with a detachable sensing transducer on a human finger in accordance with embodiments of the present disclosure.
Figure 18:
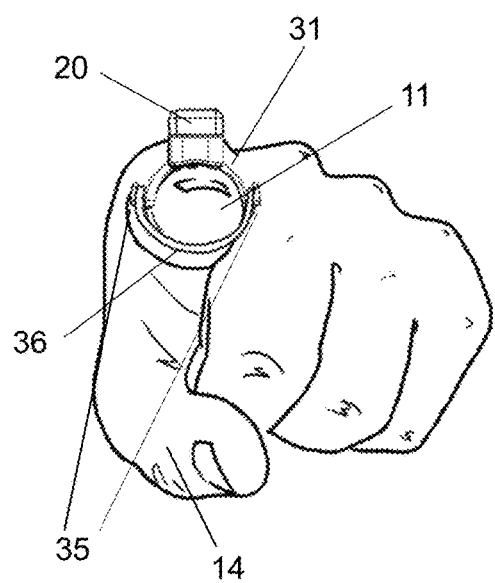
FIG. 18 shows a side view illustrating a hand-wearable ring component with a detachable sensing transducer on a human finger in accordance with embodiments of the present disclosure.

As shown in FIGS. 16, 17, and 18, a detachable sensing transducer 20 that is mated to a hand-wearable ring component 31 can be worn on a human finger 11 by looping an elastic band loop 36 around the finger with each end secured to an elastic band retention element 35. It will be appreciated that the ring band element 34, shown in FIG. 6, has an inner diameter D11 that is greater than the diameter of a human finger 11 or a human thumb 14 on which the ring is worn. It will be appreciated that the use of elastic band loops of different sizes permits a hand-wearable ring component to be secured to fingers or thumbs of different sizes and at different locations.

Figure 19:
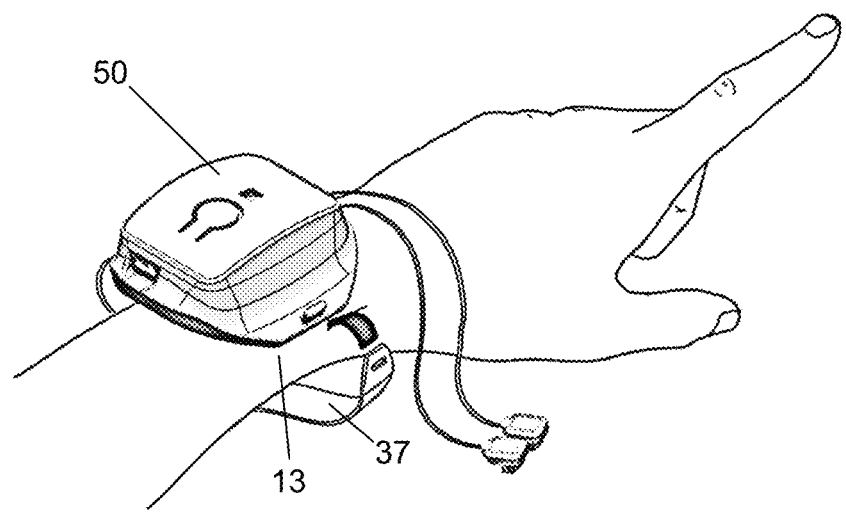
FIG. 19 illustrates the donning of hub unit of a system for tracking the movement of the hand in accordance with embodiments of the present disclosure.
Figure 20:
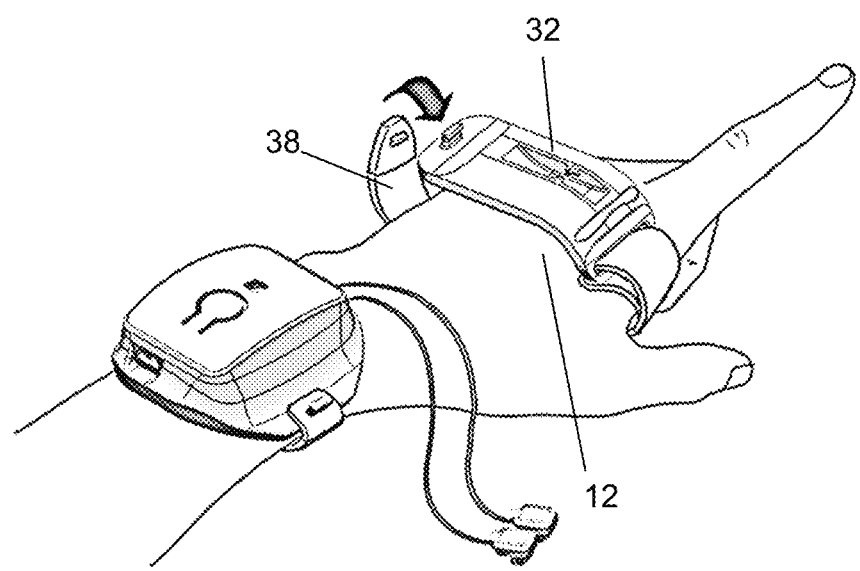
FIG. 20 illustrates the donning of a dorsal mount of a system for tracking the movement of the hand in accordance with embodiments of the present disclosure.

As shown in FIG. 19, the hub unit 50 can be secured to a human wrist 13 using a wrist strap 37. As shown in FIG. 20, a hand-wearable dorsal mount component 32 can be secured on the dorsal interosseous region of the human hand human hand 12 using a hand strap 38.

Figure 21:
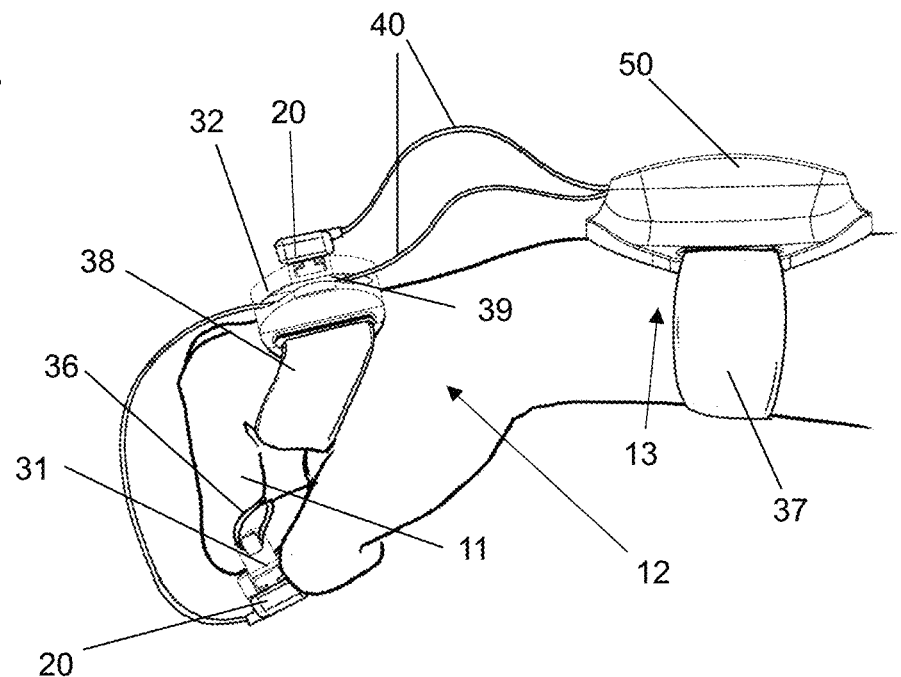
FIG. 21 illustrates a hand making a first while wearing a system for tracking the movement of the hand in accordance with embodiments of the present disclosure.

As shown in FIG. 21, the hub unit 50 secured to a human wrist 13 using a wrist strap 37, for example, and can be communicatively coupled to detachable sensing transducers 20 through wiring harness 40. It will be appreciated that the length of the wiring harness will be sufficient to allow the human hand to freely open and close when the sensing transducers 20 are mated to hand-wearable ring component 31 secured to a human finger 11 using elastic band loop 36 and the hand-wearable dorsal mount component 32 secured on the dorsal interosseous region 12 of the human hand using a hand strap 38. It will be appreciated that, by allowing a cable used in the wiring harness 40 to slide freely while being held proximal to the hand-wearable dorsal mount component 32 by a cable retention channel 39, the cable will be kept in place while allowing the a human finger 11 and a human wrist 13 to freely flex and extend.

Figure 22:
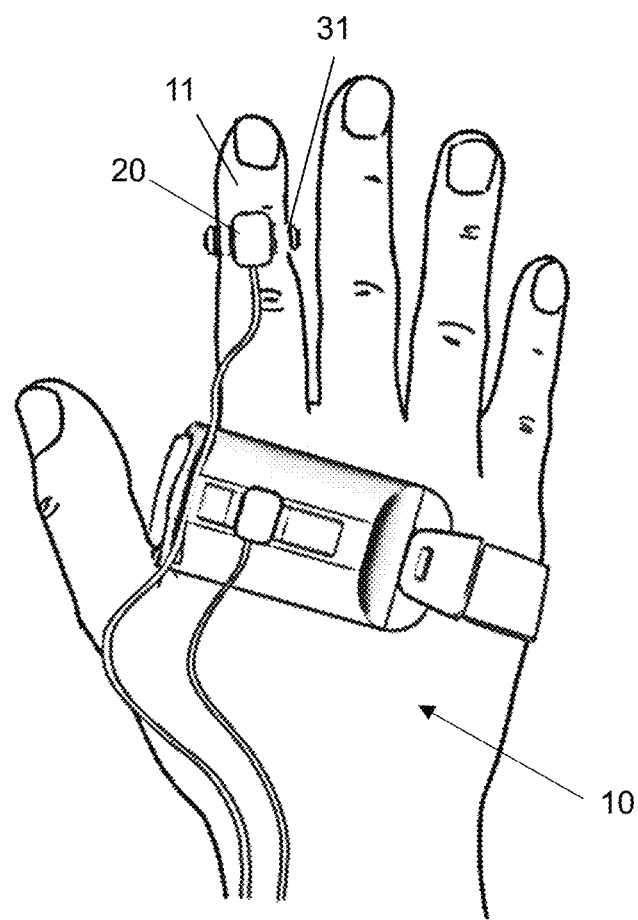
FIG. 22 shows a dorsal view of a human hand wearing a system for tracking the movement of the hand in accordance with embodiments of the present disclosure.
Figure 23:
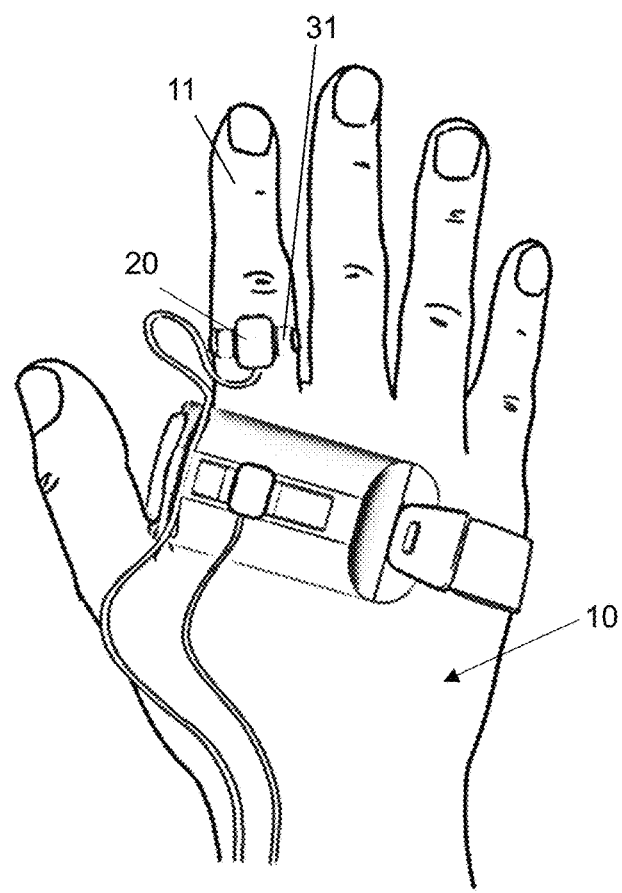
FIG. 23 illustrates an alternate placement of a hand-wearable ring component on a human finger in accordance with embodiments of the present disclosure.
Figure 24:
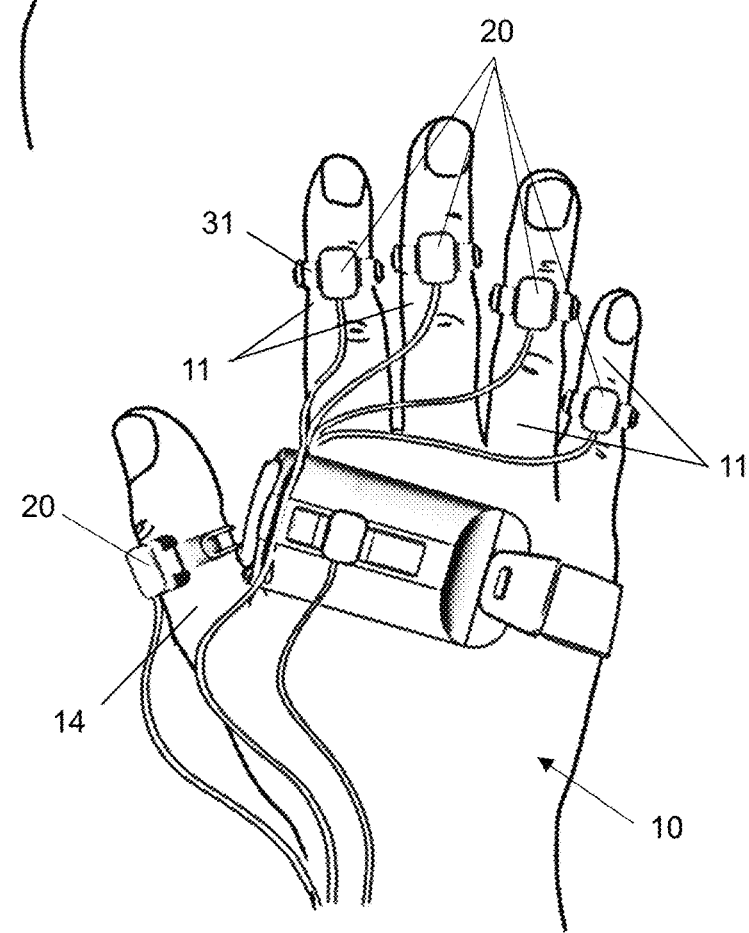
FIG. 24 shows an alternate embodiment of a system for tracking the movement of the hand in accordance with the present disclosure comprising multiple hand-wearable ring components on multiple fingers on a human hand.

As shown in FIGS. 22, 23, and 24, a hand-wearable ring component 31 can be used to secure one or a plurality of detachable sensing transducers 20 to any combination of the proximal, intermediate, and distal phalanges of the human fingers 11 and the human thumb 14 on a human hand 10. It will be appreciated that multiple detachable sensing transducers can be placed on different phalanges of the same finger or thumb.

Figure 25:
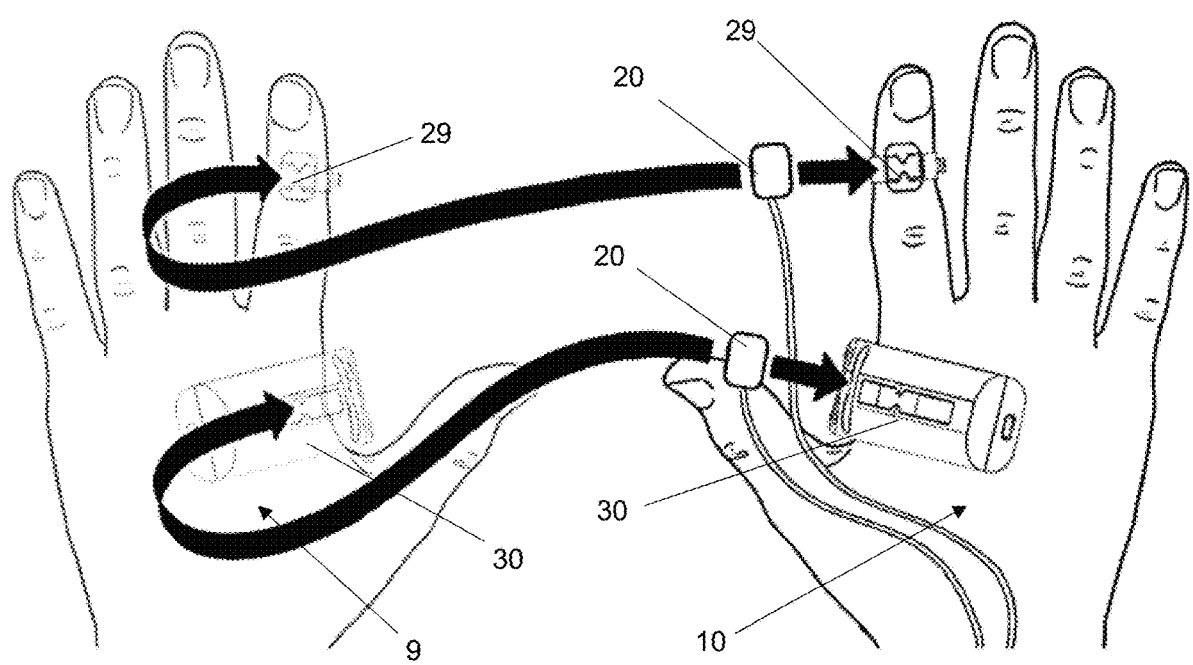
FIG. 25 illustrates the mating of detachable sensing transducers with hand-wearable components worn alternatively on the right or left hand.

As shown in FIG. 25, detachable sensing transducers 20 can be secured to either the right 10 or left 9 human hand using hand-wearable components 29, 30. It will be appreciated that a system for tracking the movement of a human hand can thus be used for tracking either the right or left hand (i.e., the system is ambidextrous).

Figure 26:
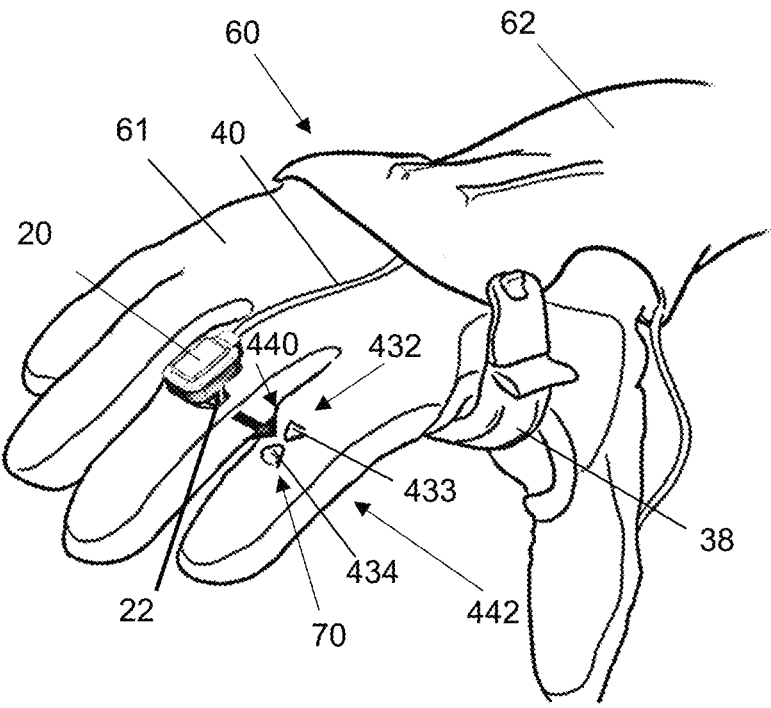
FIG. 26 illustrates the mating of a detachable sensing transducer with an interlocking clip to an interlocking hook on a hand-wearable glove in accordance with embodiments of the present disclosure.

As shown in FIGS. 26, 27, 28, and 29, certain exemplary embodiments of a device and/or system for tracking the movement of the human hand can include one or more detachable sensing transducers 20 secured to a hand-wearable glove 60. As shown in FIG. 26, hand-wearable components in a device and/or system for tracking the movement of the human hand can include a hand-wearable glove 60 that includes a glove liner 61 and a wrist-immobilizing splint 62. The hand-wearable glove 60 can be formed with one or a plurality of interlocking hooks 432 having hook elements 433, 434 similar to hook elements 233, 234 in FIGS. 6 and 9. At least one of the interlocking hooks 432 on the glove can be provided on a finger of the glove to form a finger sensor mount 70 to which a detachable sensing transducer 20 can be secured. It will be appreciated that interlocking hooks 432 can be located on a glove liner 61 adjacent to the proximal, intermediate, or distal phalanges of the human fingers and the human thumb, and/or to any other location on the human hand. It will further be appreciated that interlocking hook 432 can be located at any location on a wrist-immobilizing splint 62. The interlocking hook(s) 432 in a glove can be fabricated from plastic, metal, or any other suitable material. The glove can be fabricated from fabric and hooks can be integrated into the glove using any combination of stitching, glue, or any other suitable method. The hook 432 on glove 60 can be considered as having multiple sides 440, 441 for entry of the sensing transducer, which contributes to its ease of use and versatility.

Figure 27:
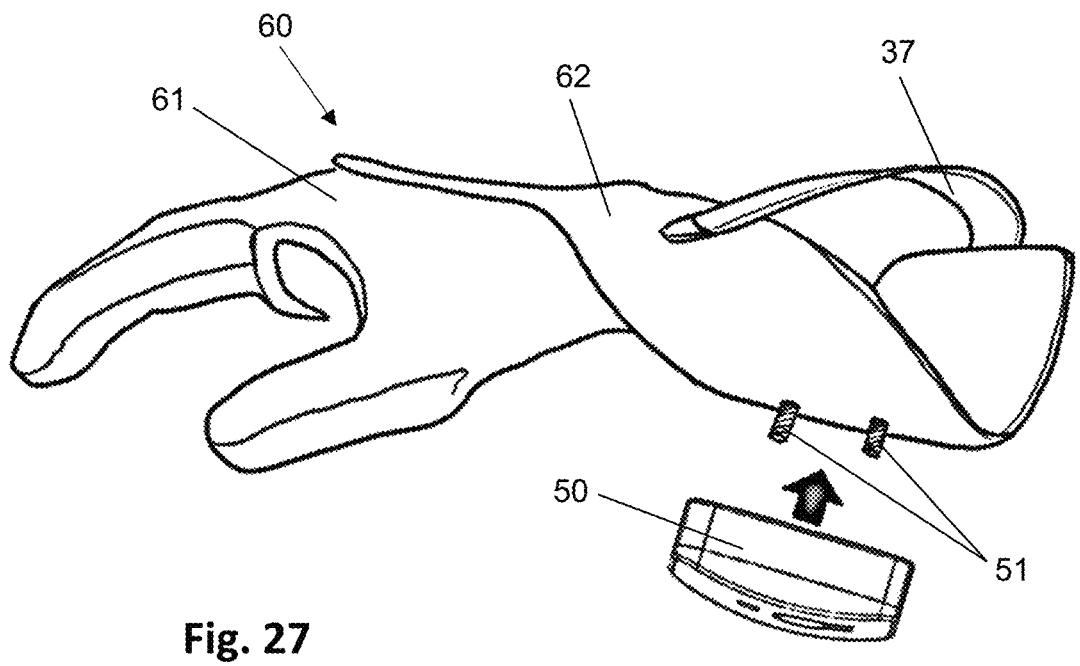
FIG. 27 illustrates the attachment of hub unit to a wrist-immobilizing splint of a system for tracking the movement of the hand in accordance with embodiments of the present disclosure.
Figure 28:
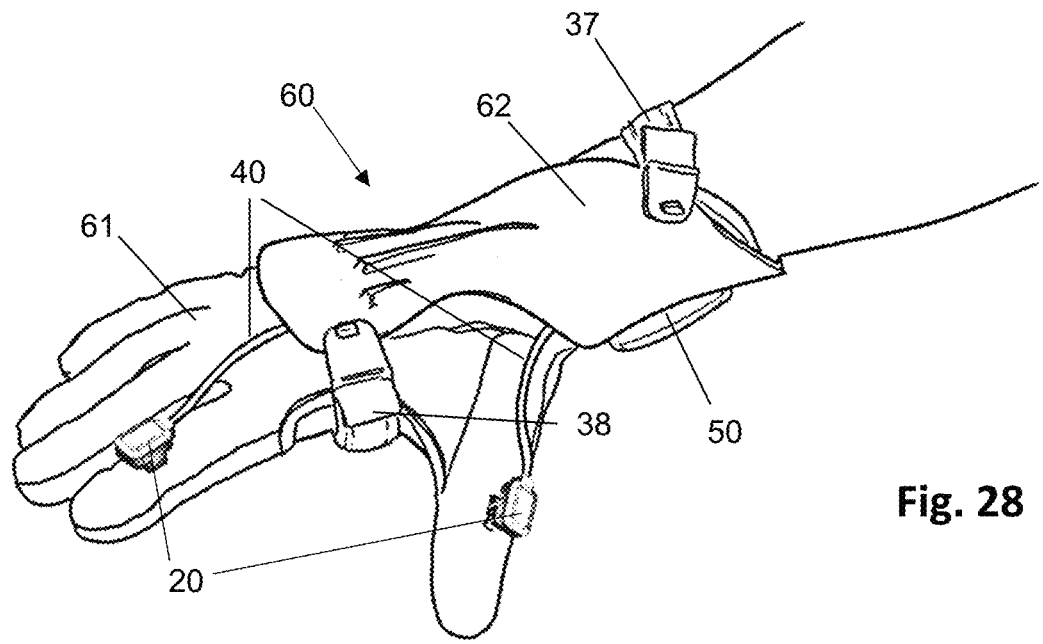
FIG. 28 shows a perspective view of a system for tracking the movement of the hand in accordance with an alternative embodiment of the present disclosure in which a hand-wearable component is a glove.
Figure 29:
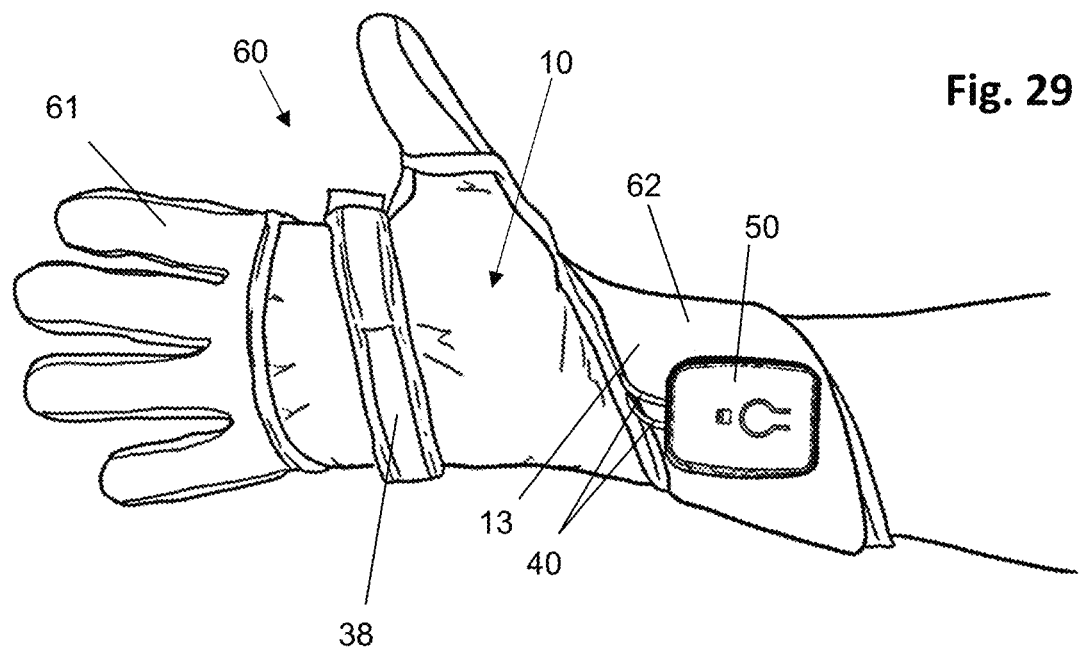
FIG. 29 shows a palm-facing view of a system for tracking the movement of the hand in accordance with an alternative embodiment of the present disclosure in which a hand-wearable component is a glove.

As shown in FIG. 26, a detachable sensing transducer 20 with an interlocking clip 22 can be inserted into an interlocking hook 432 between hook elements 433, 434 to secure the detachable sensing transducer 20 to the glove 60. As shown in FIG. 27, a hub unit 50 can be secured to the wrist-immobilizing splint 62 using threaded screws 51 or other similar attachment mechanism. A wrist strap 37 and a hand strap 38 can be used to secure the wrist-immobilizing splint 62 to the human hand. A wiring harness (40 in FIGS. 26, 28 and 29), secured between the wrist-immobilizing splint 62 and the glove liner 61, can communicatively couple the sensing transducers to the hub unit 50. The glove liner 61 can be formed from fabric, rubber, or any other flexible material. The wrist-immobilizing splint 62 can be formed from plastic, rubber, metal, or any other material that provides stiffness to support the human wrist.

Figure 30:
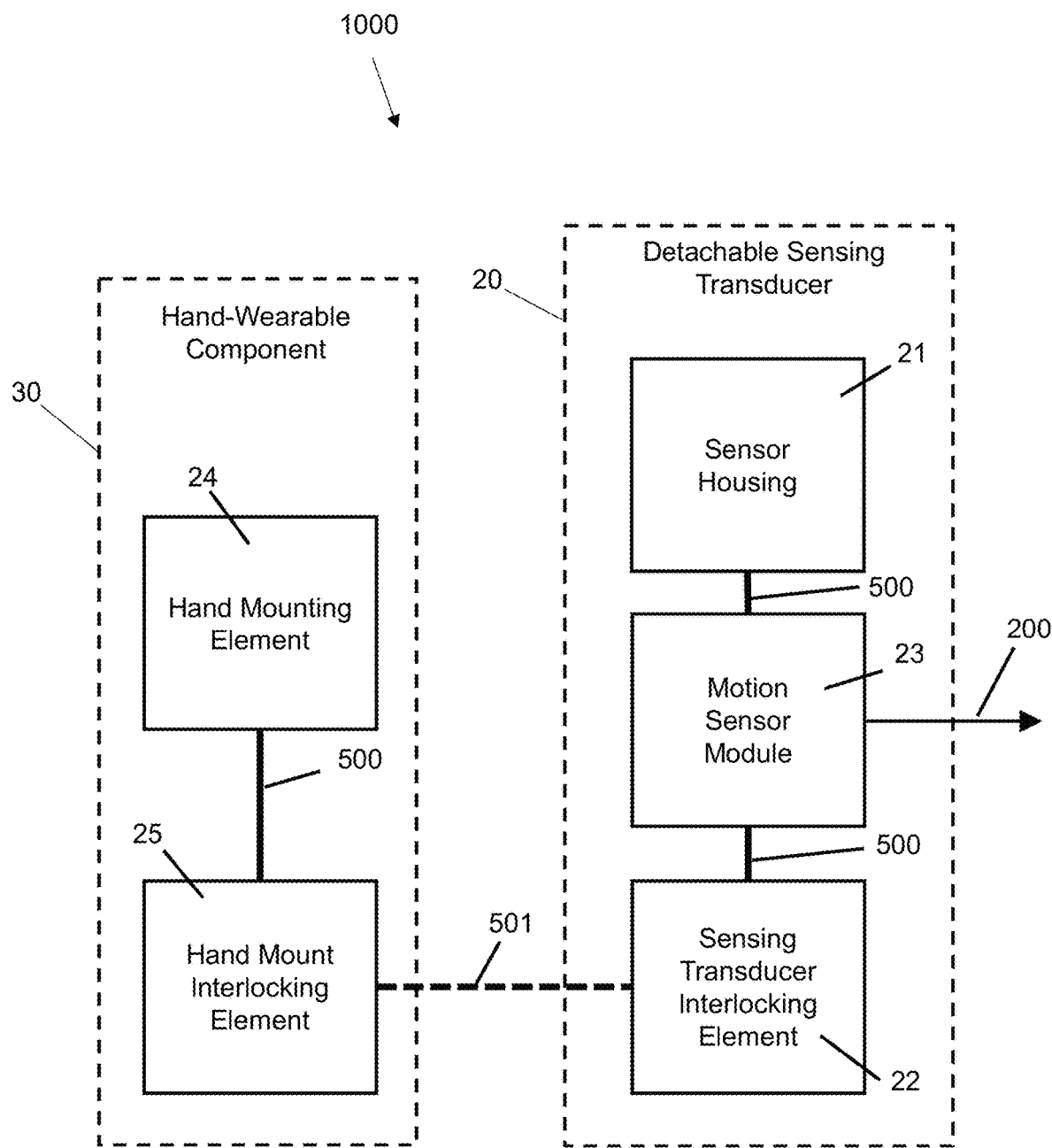
FIG. 30 is a schematic diagram of an exemplary device in accordance with the present disclosure.

FIG. 30 shows a schematic view of a device 1000 for securely attaching sensors to the human hand in accordance with embodiments of the present disclosure, wherein the device includes a detachable sensing transducer 20 and a hand-wearable component 30. The detachable sensing transducer 20 can be formed with a motion sensor module 23 and a sensing transducer interlocking element 22 that are connected via a rigid mechanical connection 500 within a sensor housing 21, also illustrated in FIGS. 2 through 5. The motion sensor module 23 can be a Bosch BMF055 9-axis motion sensor module (which includes a triaxial 14-bit accelerometer, a triaxial 16-bit gyroscope, and a triaxial geomagnetic sensor) to provide sensor measurements of the orientation, rotational velocity, and translational acceleration of the detachable sensing transducer through an inter-integrated circuit (I2C) data link 200.

The hand-wearable component 30 can be formed with a hand mounting element 24 for securing the hand-wearable component 30 to a human hand that is connected via a rigid mechanical connection 500 to a hand mount interlocking element 25. The hand mount interlocking element 25 can be formed to detachably interlock with a sensing transducer interlocking element 22, as indicated by the dashed line 501. In certain exemplary embodiments, the sensing transducer interlocking element 22 can be an interlocking clip formed to detachably interlock with the hand mount interlocking element 25 on a hand-wearable component as described elsewhere herein. In certain exemplary embodiments, the hand mount interlocking element 25 can be an interlocking hook 33, 333, 432 as described elsewhere herein. In certain exemplary embodiments, the hand-wearable component 30 can be a hand-wearable ring component, a hand-wearable dorsal mount component, or a hand-wearable glove, as described elsewhere herein. The secure retention of sensing transducer 20 within the hand mount interlocking element 25 so as to restrict rotational and translational movement of the sensing transducer 20 with respect to the hand mount interlocking element 25 as described elsewhere herein assists in gathering accurate movement data when the human wearing the hand-wearable component 30 moves the hand-wearable component 30 as part of therapeutic training, for example.

Figure 31:
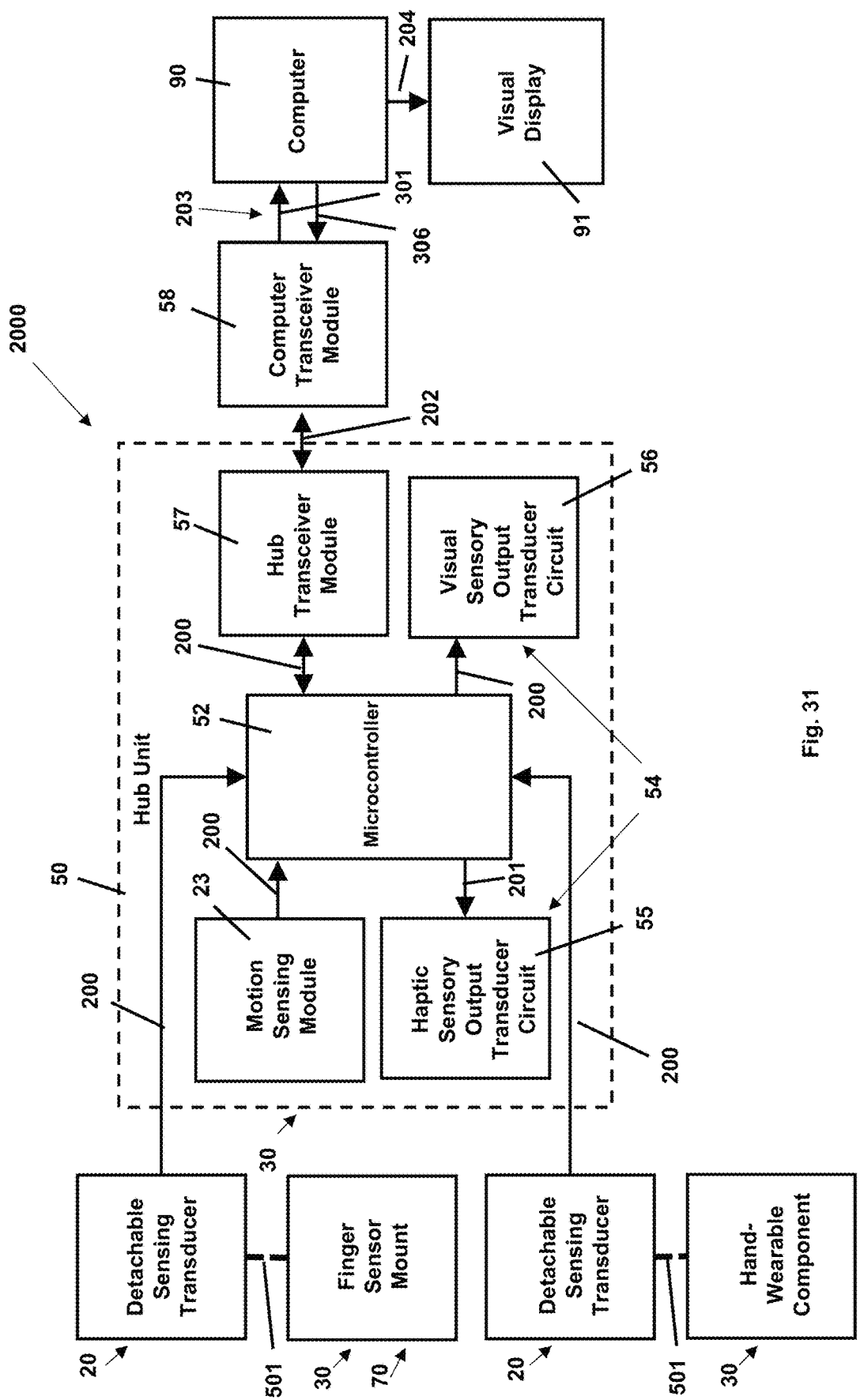
FIG. 31 is a schematic diagram of an exemplary system in accordance with the present disclosure.

FIG. 31 shows a diagram of a system 2000 in accordance with embodiments of the present disclosure, wherein the system includes detachable sensing transducers 20 and hand-wearable components 29, 30, at least one of which is a finger sensor mount 70 worn on a human finger. The hub unit 50 can house components of a movement interpretation circuit that can include a microcontroller 52 (for example, a 32-bit Nordic microcontroller) and a motion sensor module 23 that provides sensor measurements to the microcontroller 52 through an I2C data link 200.

The hub unit 50 can house sensory output transducer circuits 54 to provide sensory feedback to a human. Sensory output transducer circuits 54 can include a haptic sensory output transducer circuit 55 and a visual sensory output transducer circuit 56. In various embodiments, a visual sensory output transducer can be a graphical display of the state of the virtual world produced by a visual display such as a high definition television or a virtual reality headset, for example. A visual sensory output transducer can also be an RGB LED, for example. A haptic sensory output transducer can be an ERM vibrotactile motor or a linear resonant actuator (LRA) vibrotactile motor, for example. The haptic sensory output transducer circuit 55 can be formed from a haptic driver IC, such as a Texas Instruments DRV2603 haptic driver IC, and a vibrotactile motor, such as an ERM vibrotactile motor. The microcontroller 52 can be communicatively coupled to the haptic driver IC by a pulse width modulated (PWM) signal 201 that determines the electrical current provided to the vibrotactile motor. The vibrotactile motor can be mechanically coupled to the hub unit 50 outer housing to transmit vibrations that can be perceived by a human wearing the hub unit 50. The visual sensory output transducer circuit 56 can be formed from a LED display driver IC, such as a Linear Technology (LTC) 3219 multi-display driver IC, and an RGB LED that emits colored light that can be seen by a human. The display driver IC can be communicatively coupled to the microcontroller 52 through an I2C data link 200 which the microcontroller 52 uses to command pulses by the RGB LEDs of specified number, color, intensity, duration, and inter-pulse delay.

The hub unit 50 can house a hub transceiver module 57, such as a Bluetooth v5.0 transceiver module, for example, which can be communicatively coupled to the microcontroller 52 through either a serial data link 200 or a memory-mapped interface for a transceiver included within the microcontroller. The hub transceiver module 57 can be communicatively coupled to a computer transceiver module 58 through a wireless data link 202, for example a Bluetooth radio frequency data link. The computer transceiver module 58 can be a Bluetooth Universal Serial Bus (USB) module, such as a Laird USB BL654, for example, that is communicatively coupled to a computer 90 through a serial data link 203, which can be a USB serial data link, for example. It will be appreciated that these data links allow a system for tracking the movement of the human hand to wirelessly transmit sensor measurement data 301 to the computer 90 and to wirelessly receive sensory output commands 306 from the computer 90. The computer 90 can provide graphical data to the visual display 91 through a video data link 204. The visual display 91 can provide graphical information to a human that is wearing the hand-wearable components 30. The visual display 91 can be a high-definition television monitor or a virtual reality headset, for example.

Figure 32:
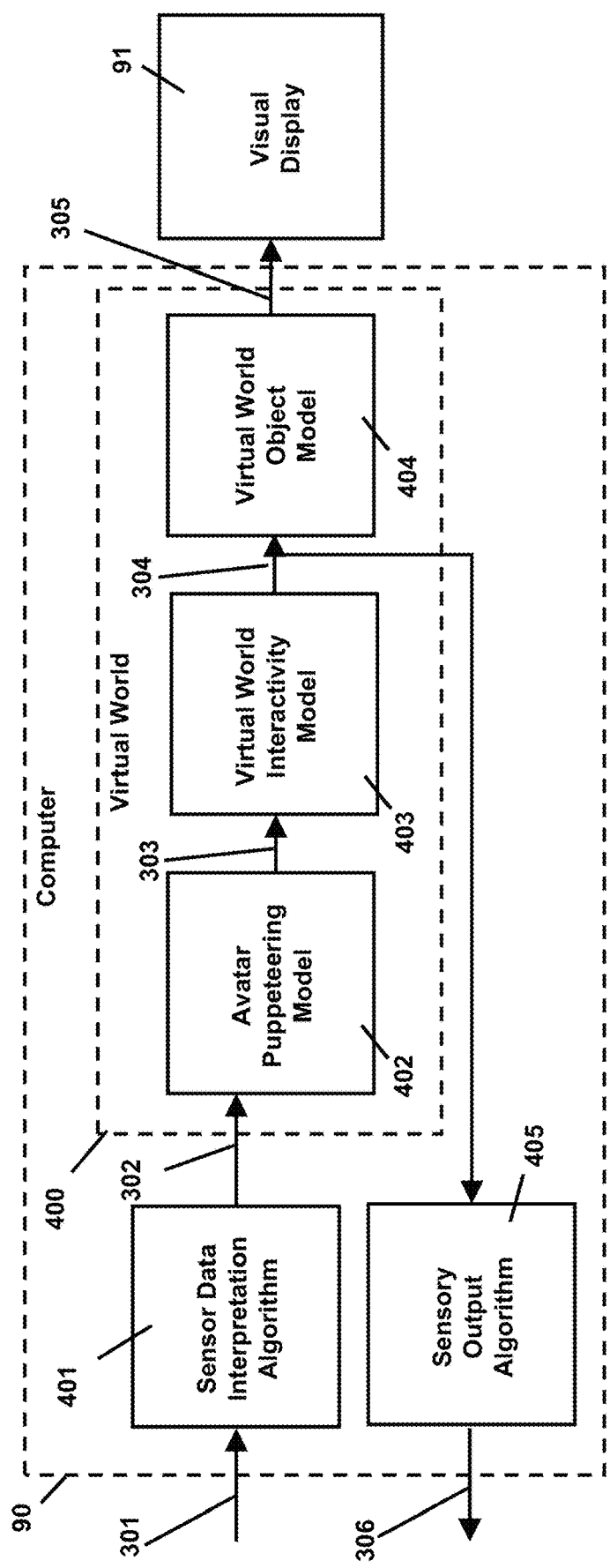
FIG. 32 is a schematic diagram of a computer-implemented method of human UE therapy.
Figure 34:
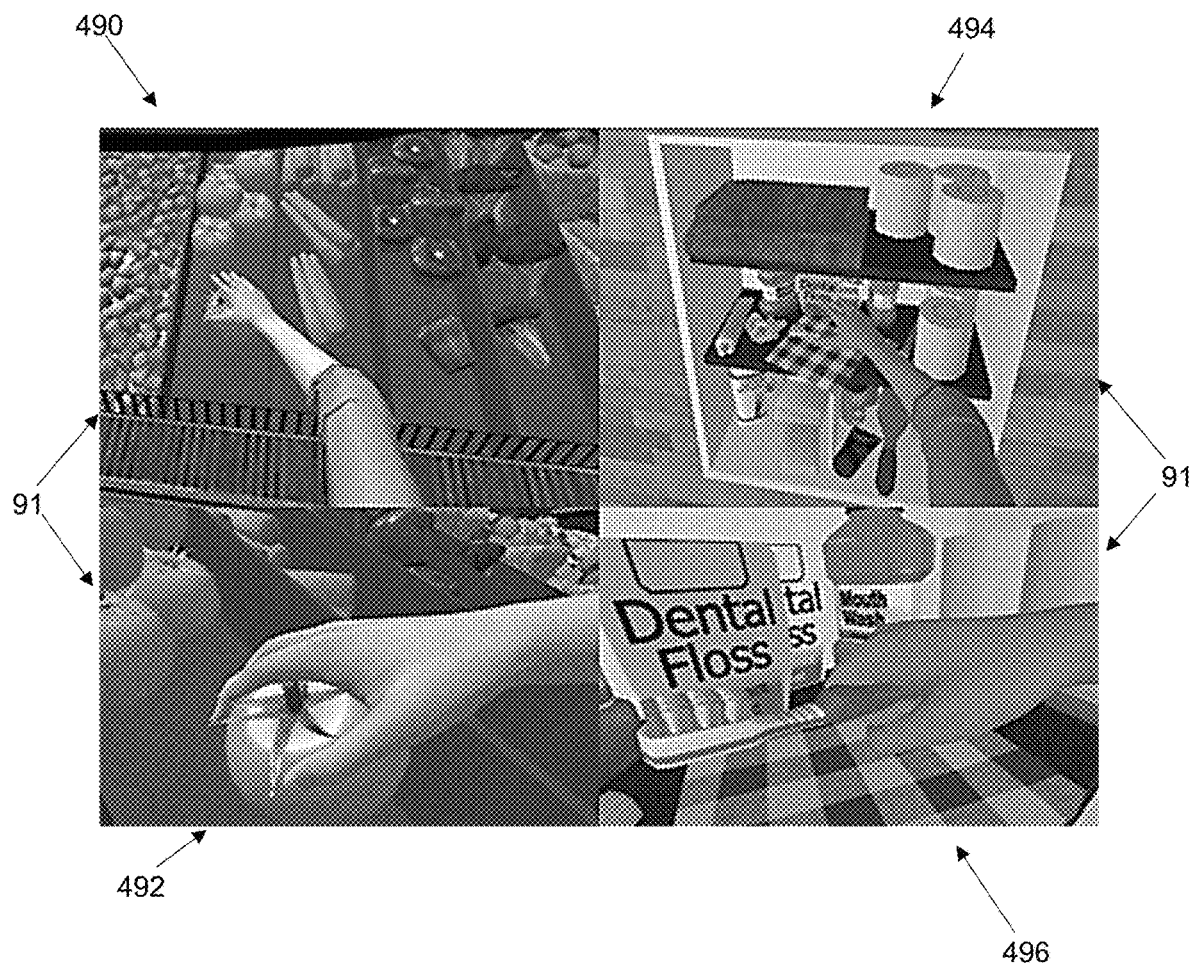
FIG. 34 shows exemplary embodiments of different visual displays in accordance with the present disclosure.

FIG. 32 is a diagram illustrating how a system for tracking the movement of the hand can be used in a computer-implemented method of human UE therapy in accordance with embodiments of the present disclosure. As shown in FIG. 32, sensor measurement data 301 provided to computer 90 by a serial data link can be processed by a sensor data interpretation algorithm 401 to produce human kinematic state estimates 302. In various embodiments, the sensor data interpretation algorithm can be an Unscented Kalman Filter algorithm that includes a twenty-seven degrees of freedom hand articulation model and which produces human kinematic state estimates that include estimated joint angle, joint angular rate, joint position, and joint velocity for each joint of the hand that lies between a pair of motion sensor modules. The joints of the hand can include the joints of the fingers, thumb, and wrist. Sensor measurement data 301 can include the measured orientation, rotational velocity, and translational acceleration of each sensing transducer at the location of a hand-wearable component on a human hand, as described elsewhere herein. Human kinematic state estimates 302 can include estimated joint angle, joint angular rate, joint position, and joint velocity for each joint of the hand that lies between a pair of motion sensor modules, which can include the joints of the fingers, thumb, and wrist. An avatar puppeteering model 402 can interpret human kinematic state estimates 302 as the kinematic state of a human avatar 303. The kinematic state of a human avatar 303 can be interpreted by a virtual world interactivity model 403 as virtual object interactions 304. Virtual object interactions 304 can be provided to a virtual world object model 404 which maintains the state of a virtual world 305, which includes the kinematic state of a human avatar 303 and the state of all other virtual objects. It will be appreciated that a virtual world interactivity model 403 and a virtual world object model 404 can be constructed to produce therapeutic interactions between a human and a collection of interactive objects within a virtual world 400 that result in exercising the human UE. Examples of virtual object interactions 304 between a human avatar and objects in the virtual world can include picking up an object, translating an object, rotating an object, placing an object, dropping an object, throwing an object, and squeezing an object. Such interactions can be processed by a virtual world object model 404 to produce changes in the state of the virtual world 305 which can include changes in the position, velocity, orientation, and depiction of virtual objects. Changes to the state of the virtual world 305 can further include secondary effects such as the filling of a virtual glass with water, a piece of virtual food being consumed, or the reaction of a non-player character (such as a virtual pet) in the virtual world. The state of the virtual world 305 can be communicated to a visual display 91 through a video data link to provide graphical information to a human. For example, as shown at 490 and 492 in FIG. 34, a user is selecting and grabbing a tomato from a refrigerator as represented in the different visual displays 91. As shown at 494 and 496, a user is selecting a grabbing a toothbrush as represented in the different visual displays 91.

It will be appreciated that a method in accordance with the present disclosure can further involve providing a device including multiple hand-wearable components (e.g., any combination of one or more ring components, dorsal mount component, glove, glove liner and/or hub unit) and a sensing transducer detachably secured to at least one of the plurality of hand-wearable components. The sensing transducer may not be detachably secured to a hub unit, but can be detachably secured to any of the ring components, the dorsal mount component, glove or glove liner, for example. The exemplary method can further sense the movement of a human hand wearing the multiple hand-wearable components via the sensing transducer. The exemplary method can further convey the sensed movement of the hand to a computing device (e.g., hub unit 50 or computer 90) and execute, by the computing device, instructions stored in a memory to display movement of a virtual object on a visual display based on the sensed movement.

Virtual object interactions 304 can be provided to a sensory output algorithm 405 to generate sensory output commands 306 that include visual sensory output commands specifying the number, color, intensity, duration, and inter-pulse delay of LED light effects to be rendered by a visual sensory output transducer circuit and haptic sensory output commands specifying the number, frequency, intensity, duration, and inter-pulse delay of vibrotactile effects to be rendered by a haptic sensory output transducer circuit. For example, in response to a virtual object interaction involving the hand of a human avatar picking up a virtual object, a sensory output algorithm 405 can generate a haptic sensory output command that results in two 500 millisecond vibrotactile pulses being generated by an ERM vibrotactile motor. The vibrotactile pulses can be perceived by a human wearing a hub unit (e.g., 50) that includes the ERM vibrotactile motor.

Figure 33:
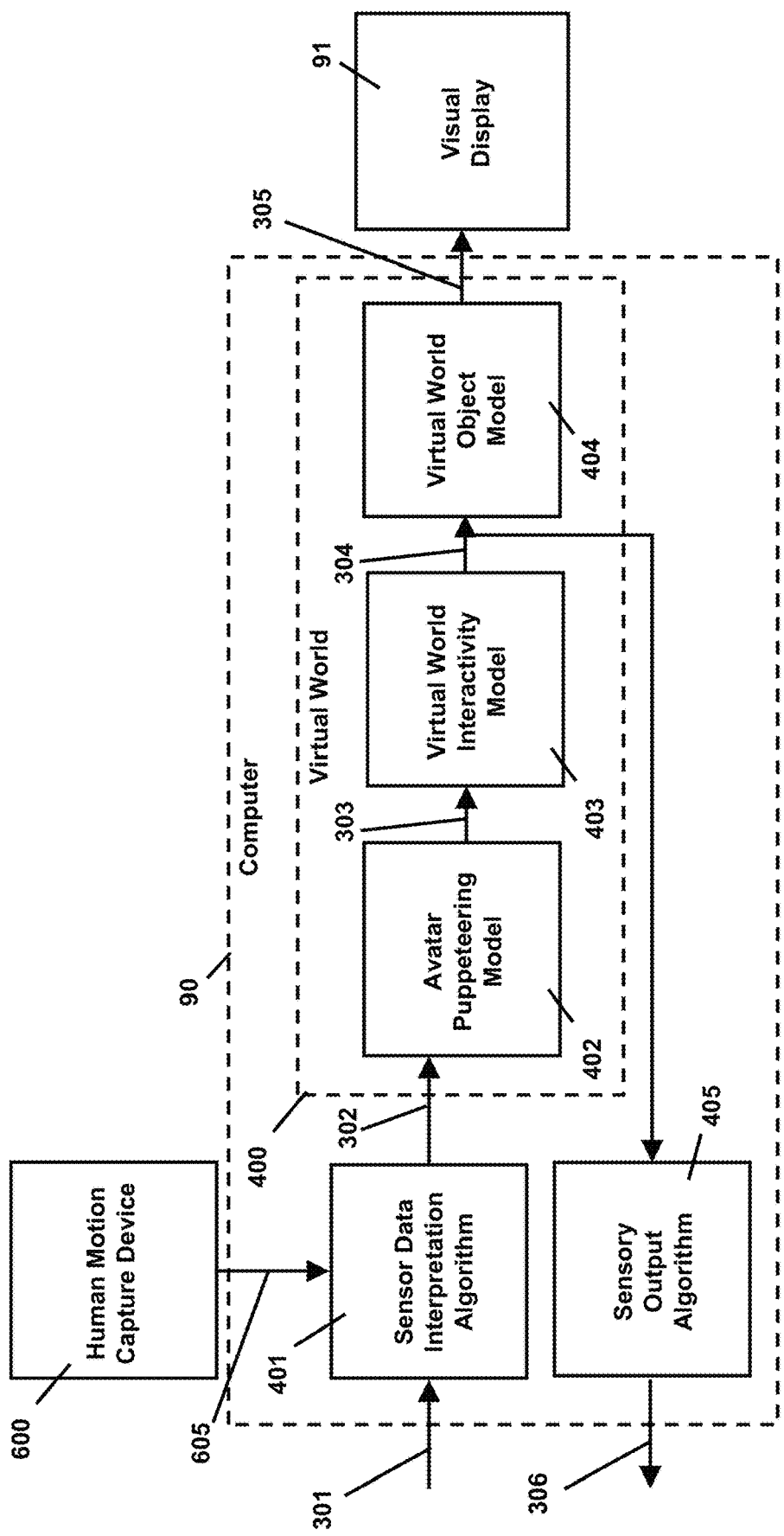
FIG. 33 is a schematic diagram of a computer-implemented method of human UE therapy that includes a human motion capture device.

As shown in FIG. 33, a system in accordance with embodiments of the present disclosure can be employed in a system that includes a sensing transducer (hereafter referred to as a human motion capture device 600) operatively configured to sense the kinematic state of the user's arm and hand, and to transmit human motion capture data 605 to a sensor data interpretation algorithm 401. In certain exemplary embodiments, the human motion capture device 600 can include a depth sensor camera and skeletal tracking software. The depth sensor camera can be a Microsoft Kinect™ for Xbox 360™, Microsoft Kinect™ for Xbox One™, a Microsoft Azure Kinect™, or an Intel Realsense™ depth camera, for example. The skeletal tracking software can be a Kinect SDK™, Nuitrack™ Full Body Skeletal Tracking Software, or a Cubemos™ Skeleton Tracking SDK, for example. In various embodiments, sensor measurement data 301 and human motion capture data 605 can be processed by a sensor data interpretation algorithm 401 to produce human kinematic state estimates 302 that include estimated joint angles, joint angular rates, joint positions, and joint velocities for joints of the human arm (shoulder and elbow), in addition to the joints of the hand that lie between pairs of motion sensor modules. Other interactions, commands, models, worlds and communications in FIG. 33 can be as described with respect to FIG. 32 above.

A sensor mounting system in accordance with the present disclosure can be represented as a hand-wearable device or devices in any form such as described elsewhere herein. For example, the sensor mounting system can be one or more ring components or finger sensor mounts, a dorsal mount component, a glove, a glove orthosis, a glove liner or any combination of such components and devices, wherein such components and/or devices include suitable mounting structure to detachably receive a sensor as described herein. The hub unit 50 can be a hand-wearable device provided as part of a sensor mounting system in accordance with aspects of the present disclosure. However, in various embodiments, no sensing transducer is secured to the hub unit 50. In embodiments involving a glove orthosis, the glove orthosis can include a finger sensor mount integrated in a glove liner and a wrist-immobilizing splint integrated with the glove liner, for example. The sensor mounting system can be combined with the movement interpretation circuit including sensing transducers detachably securable to one or more of the hand-wearable components of the sensor mounting system such as described elsewhere herein, wherein each sensing transducer is communicatively coupled to a computing device executing programming that interprets the movements of each sensing transducer as the movement of a human finger or a human hand. In embodiments involving a glove orthosis, a sensing transducer can be detachably securable to the finger sensor mount one or more sensing transducers can be detachably securable to the wrist-immobilizing splint. The programming can automatically interpret the sensed movement of the human finger or the human hand as movements of a human avatar in a virtual world, for example.

The above-described embodiments of the present disclosure may be implemented in accordance with or in conjunction with one or more of a variety of different types of systems, such as, but not limited to, those described below.

The present disclosure contemplates a variety of different systems each having one or more of a plurality of different features, attributes, or characteristics. A "system" as used herein refers to various configurations of: (a) one or more hand-wearable devices or sensor mounting systems employing one or more microcontrollers and/or one or more sensors; (b) one or more computing devices, such as a desktop computer, laptop computer, tablet computer, personal digital assistant, mobile phone, or other mobile computing device; (c) one or more output devices, such as a display device; (d) one or more sensor devices in communication with one or more microcontrollers; (e) one or more hand-wearable devices or sensor mounting systems communicatively coupled to one or more computing devices; (f) one or more hand-wearable devices or sensor mounting systems communicatively coupled to one or more output devices, such as a display device; (g) one or more hand-wearable devices or sensor mounting systems communicatively coupled to one or more computing devices and one or more output devices, such as a display device.

In certain embodiments in which the system includes a computing device in combination with a hand-wearable device or sensor mounting system, the computing device includes at least one processor configured to transmit and receive data or signals representing events, messages, commands, or any other suitable information between the computing device and the hand-wearable device or sensor mounting system. The processor of the computing device is configured to execute the events, messages, or commands represented by such data or signals in conjunction with the operation of the computing device. Moreover, the processor of the hand-wearable device or sensor mounting system is configured to transmit and receive data or signals representing events, messages, commands, or any other suitable information between the hand-wearable device or sensor mounting system and the computing device. The microprocessor of the hand-wearable device or sensor mounting system is further configured to execute the events, messages, or commands represented by such data or signals in conjunction with the operation of the hand-wearable device or sensor mounting system and one or more sensors secured thereto.

In embodiments in which the system includes a computing device configured to communicate with a hand-wearable device or sensor mounting system through a data network, the data network is a local area network (LAN), a wide area network (WAN), a public network such as the Internet, or a private network. The hand-wearable device or sensor mounting system and the computing device are configured to connect to the data network or remote communications link in any suitable manner. In various embodiments, such a connection is accomplished for the computing device via: a conventional phone line or other data transmission line, a digital subscriber line (DSL), a T-1 line, a coaxial cable, a fiber optic cable, a wireless or wired routing device, a mobile communications network connection (such as a cellular network or mobile Internet network), or any other suitable medium. In various embodiments, such a connection is accomplished for the computing device via a wireless routing device.

It will be appreciated that any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing, including a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented as entirely hardware, entirely software (including firmware, resident software, micro-code, etc.) or as a combined software and hardware implementation, all of which may be generally referred to herein as a "circuit," "module," "component," or "system." Furthermore, aspects of the present disclosure may take the form of a computer program product embodied in one or more computer readable media having computer readable program code embodied thereon.

It will be appreciated that all of the disclosed methods and procedures herein can be implemented using one or more computer programs or components. These components may be provided as a series of computer instructions on any conventional computer-readable medium, including RAM, SATA DOM, or other storage media. The instructions may be configured to be executed by one or more processors which, when executing the series of computer instructions, performs or facilitates the performance of all or part of the disclosed methods and procedures.

Unless otherwise stated, devices or components of the present disclosure that are in communication with each other do not need to be in continuous communication with each other. Further, devices or components in communication with other devices or components can communicate directly or indirectly through one or more intermediate devices, components or other intermediaries. Further, descriptions of embodiments of the present disclosure herein wherein several devices and/or components are described as being in communication with one another does not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed computers and computing devices, for example. In this regard, a processor (e.g., a microprocessor or controller device) receives instructions from a memory or like storage device that contains and/or stores the instructions, and the processor executes those instructions, thereby performing a process defined by those instructions.

Computer program code for carrying out operations for aspects of the present disclosure may be written in any combination of one or more programming languages, including an object oriented programming language such as Java, Python, JavaScript, C++, C#, Scala, Smalltalk, Eiffel, JADE, Emerald, VB.NET or the like, conventional procedural programming languages, such as the "C" programming language, Visual Basic, Fortran 2003, Perl, COBOL 2002, PHP, ABAP, dynamic programming languages such as Python, MATLAB, Ruby and Groovy, or other programming languages. The program code may execute entirely on an external computing device, entirely on a hub unit, as a stand-alone software package, partly on an external computing device and partly on a hub unit.

Where databases are described or contemplated in the present disclosure, it will be appreciated that various memory structures besides databases may be readily employed. Any drawing figure representations and accompanying descriptions of any exemplary databases presented herein are illustrative and not restrictive arrangements for stored representations of data. Further, any exemplary entries of tables and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art. Appropriate encryption and other security methodologies can also be employed by the system of the present disclosure, as will be understood to one of ordinary skill in the art.

Aspects of the present disclosure are described herein with reference to flowchart illustrations and/or block diagrams of methods, apparatuses (e.g., devices and systems) and computer program products according to embodiments of the disclosure. It will be understood that each block of the flowchart illustrations and/or block diagrams, directional arrows between blocks and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The invention claimed is:

1. A device, comprising:
a hand-wearable component comprising a hook, wherein the hook comprises a pair of opposing hook elements separated by a gap having a gap width; and
a sensing transducer detachably securable to the hook, wherein the sensing transducer comprises a sensor housing and a clip, wherein the clip comprises a neck portion comprising a neck portion width that is smaller than the gap width such that the neck portion is configured to pass through the gap between the pair of opposing hook elements as the sensing transducer is detachably secured to the hook.

2. The device of claim 1, wherein the clip further comprises a back wall, wherein the back wall extends from a head portion of the clip to a base portion of the clip and comprises a back wall width that is greater than the gap width.

3. The device of claim 1, wherein the clip further comprises a base portion, and wherein the base portion comprises a base portion width that is wider than the gap width.

4. The device of claim 1, wherein the neck portion comprises a first side wall and a second side wall, wherein the first side wall is substantially planar, and wherein the second side wall comprises a leading segment, a trailing segment and a knob extending outwardly from the second side wall between the leading segment and the trailing segment.

5. The device of claim 4, wherein the knob has a crest comprising a crest width extending from the first side wall to the crest, and wherein the crest width is larger than the gap width.

6. The device of claim 3, wherein the hook comprises a floor surface and opposing side walls, wherein the hook elements, the floor surface and the opposing side walls form a slot comprising a slot width, and wherein the base portion width is less than the slot width.

7. The device of claim 6, wherein the slot comprises a slot height and wherein the clip base portion comprises a base portion height that is less than the slot height.

8. The device of claim 1, wherein the clip further comprises a head portion having a bottom surface, wherein each of the pair of opposing hook elements has a top surface, and wherein the clip head portion bottom surface slidingly engages the top surfaces of each of the pair of opposing hook elements as the sensing transducer is detachably secured to the hook.

9. The device of claim 1, wherein the hand-wearable component is a dorsal mount operatively configured to be worn on a human hand, wherein the hook comprises a first side and a second side, and wherein the sensing transducer is detachably securable from the first side of the hook and detachably securable from the second side of the hook.

10. The device of claim 1, wherein the hand-wearable component is a ring component configured to be worn on a human finger, wherein the hook comprises a first side and a second side, and wherein the sensing transducer is detachably securable from the first side of the hook and detachably securable from the second side of the hook.

11. The device of claim 1, wherein the hand-wearable component is a glove, wherein the hook comprises a first side and a second side, and wherein the sensing transducer is detachably securable from the first side of the hook and detachably securable from the second side of the hook.

12. The device of claim 1, wherein the sensing transducer comprises a motion sensor module comprising at least one of: an accelerometer, a gyroscope, and a magnetometer.

13. A system, comprising:
a hand-wearable sensor mounting system comprising a plurality of hand-wearable components; and
a movement interpretation circuit, wherein the movement interpretation circuit comprises a plurality of sensing transducers, wherein each of the plurality of sensing transducers is communicatively coupled to a computing device executing programming that interprets movements of each of the plurality of sensing transducers as movement of a human finger or a human hand, wherein each of the plurality of sensing transducers is detachably securable to at least one of the plurality of hand-wearable components;
wherein at least one of the plurality of hand-wearable components comprises a hook, wherein the hook comprises a pair of opposing hook elements separated by a gap, wherein each of the plurality of sensing transducers comprises a housing, wherein the housing comprises a clip having a neck portion that is narrower than the gap width such that the neck portion can pass through the gap between the pair of opposing hook elements as it is detachably secured to the hook.

14. The system of claim 13, wherein at least one of the plurality of hand-wearable components comprises a finger sensor mount.

15. The system of claim 13, wherein at least one of the plurality of hand-wearable components comprises a glove configured to be worn on the human hand.

16. The system of claim 13, wherein at least one of the plurality of hand-wearable components comprises a hub unit comprising a microcontroller and a transceiver.

17. The system of claim 13, wherein the hand-wearable sensor mounting system comprises a glove orthosis comprising:
a finger sensor mount integrated in a glove liner; and
a wrist-immobilizing splint integrated with the glove liner,
and wherein the plurality of sensing transducers comprises a first sensing transducer detachably securable to the finger sensor mount and a second sensing transducer detachably securable to the wrist-immobilizing splint.

18. The system of claim 13, at least one of the plurality of hand-wearable components comprises a hub unit comprising a microcontroller and a transceiver, wherein at least one of the plurality of hand-wearable components comprises a finger sensor mount, and wherein at least one of the plurality of sensing transducers is detachably securable to the finger sensor mount.

19. The system of claim 18, wherein at least one of the plurality of hand-wearable components is a dorsal mount operatively configured to be worn on an interosseous region of a human hand and wherein at least one of the plurality of sensing transducers is detachably securable to the dorsal mount.

20. The system of claim 13, wherein the programming automatically interprets the movement of the human finger or the human hand as movements of a human avatar in a virtual world.

21. The system of claim 13, further comprising a human motion capture device for capturing movement of a human arm to which the human hand and human finger are attached.

22. A device, comprising:
a hand-wearable component comprising a hook;
a sensing transducer comprising a clip, wherein the clip is detachably securable to the hook and further wherein the clip is translationally and rotationally restricted by the hook when the clip is secured to the hook; and
wherein the hook comprises a pair of opposing hook elements formed with a gap therebetween, a floor surface and opposing side walls, wherein the hook elements, the floor surface and the opposing side walls form a slot comprising a slot width, and wherein the clip comprises a base portion comprising a base portion width that is less than the slot width, whereby the base portion is maintained between the opposing side walls, the floor surface and the hook elements when inserted through the slot and is thereby translationally and rotationally restricted.

23. The device of claim 22, wherein the hook comprises a first side and a second side, and wherein the clip is detachably securable from the first side of the hook and detachably securable from the second side of the hook.

* * * * *